US009443993B2

(12) United States Patent
Nakamura et al.

(10) Patent No.: US 9,443,993 B2
(45) Date of Patent: Sep. 13, 2016

(54) SPECTROSCOPIC SENSOR AND METHOD FOR MANUFACTURING SAME

(71) Applicant: SEIKO EPSON CORPORATION, Tokyo (JP)

(72) Inventors: Noriyuki Nakamura, Sakata (JP); Terunao Hanaoka, Suwa (JP); Kunihiko Yano, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/219,477

(22) Filed: Mar. 19, 2014

(65) Prior Publication Data

US 2014/0295610 A1    Oct. 2, 2014

(30) Foreign Application Priority Data

Mar. 28, 2013  (JP) .................................. 2013-068320
Mar. 29, 2013  (JP) .................................. 2013-071594

(51) Int. Cl.
*H01L 31/0216* (2014.01)
*H01L 31/02* (2006.01)
*A61B 5/1455* (2006.01)

(52) U.S. Cl.
CPC ..... *H01L 31/02165* (2013.01); *A61B 5/14552* (2013.01); *H01L 31/02024* (2013.01); *A61B 2562/0238* (2013.01); *A61B 2562/046* (2013.01); *A61B 2562/12* (2013.01); *A61B 2562/164* (2013.01)

(58) Field of Classification Search
CPC ..... G02B 5/22; G02B 5/288; G03F 7/70575; G03F 7/70958; G03F 1/144; G03F 7/70191; H01L 27/14868; H01L 31/02165
See application file for complete search history.

(56) References Cited

U.S. PATENT DOCUMENTS

| 5,592,223 | A | * | 1/1997 | Takamura et al. ............. 348/309 |
| 5,986,704 | A | * | 11/1999 | Asai et al. ..................... 348/340 |
| 6,518,860 | B2 | | 2/2003 | Ellä et al. |
| 6,830,951 | B2 | * | 12/2004 | Laurin et al. ................... 438/69 |
| 7,416,915 | B2 | * | 8/2008 | Kasano et al. ................. 438/70 |
| 7,493,713 | B2 | * | 2/2009 | Park .................................. 38/70 |
| 7,759,679 | B2 | | 7/2010 | Inaba et al. |
| 7,825,029 | B2 | | 11/2010 | Leib et al. |
| 2006/0029889 | A1 | | 2/2006 | Wang |
| 2011/0074991 | A1 | * | 3/2011 | Sakoh ........................... 348/279 |

(Continued)

FOREIGN PATENT DOCUMENTS

JP   A-08-508114   8/1996
JP   A-09-015420   1/1997

(Continued)

*Primary Examiner* — Bac Au
(74) *Attorney, Agent, or Firm* — Oliff PLC

(57) ABSTRACT

A method for manufacturing a spectroscopic sensor includes: (a) forming a light receiving element on a semiconductor substrate; (b) forming an angle restricting filter on the semiconductor substrate; and (c) forming a spectroscopic filter on the angle restricting filter. The step (c) of forming a spectroscopic filter includes: (c1) forming a first light transmitting film having a peripheral edge that overlaps a light blocking portion in plan view ox the semiconductor substrate by a lift-off method; and (c2) forming a second light transmitting film at a position spaced apart from the first light transmitting film in plan view of the semiconductor substrate by the lift-off method, the second light transmitting film having a peripheral edge that overlaps the light blocking portion in plan view of the semiconductor substrate.

5 Claims, 17 Drawing Sheets

(56) References Cited

U.S. PATENT DOCUMENTS

| | | |
|---|---|---|
| 2011/0215432 A1 | 9/2011 | Uematsu et al. |
| 2011/0216315 A1 | 9/2011 | Uematsu et al. |
| 2011/0310472 A1 | 12/2011 | Hirai et al. |
| 2013/0038824 A1* | 2/2013 | Nakanishi .................. 349/106 |
| 2014/0217625 A1* | 8/2014 | Hazart et al. ............... 264/1.7 |

FOREIGN PATENT DOCUMENTS

| | | |
|---|---|---|
| JP | A-2001-100018 | 4/2001 |
| JP | A-2002-268645 | 9/2002 |
| JP | A-2003-57567 | 2/2003 |
| JP | A-2005-527112 | 9/2005 |
| JP | A-2006-048060 | 2/2006 |
| JP | A-2006-251598 | 9/2006 |
| JP | A-2009-047768 | 3/2009 |
| JP | A-2010-186146 | 8/2010 |
| JP | A-2010-186147 | 8/2010 |
| JP | A-2011-185634 | 9/2011 |
| JP | A-2011-205088 | 10/2011 |
| JP | A-2012-123187 | 6/2012 |
| JP | A-2012-150263 | 8/2012 |
| WO | WO 95/17690 A | 6/1995 |
| WO | WO 03/088340 A | 10/2003 |
| WO | WO 2005/069376 A | 7/2005 |

* cited by examiner

SPECTROSCOPIC SENSOR AND METHOD FOR MANUFACTURING SAME

The entire disclosure of Japanese Patent Application No. 2013-068320, filed Mar. 28, 2013 and Japanese Patent Application No. 2013-071594, filed Mar. 29, 2013 is expressly incorporated by reference herein.

BACKGROUND

1. Technical Field

The invention relates to a spectroscopic sensor and a method for manufacturing the same.

2. Related Art

In the medical, agricultural and environmental fields, spectroscopic sensors are need to diagnose or examine target objects. In the medical field, for example, pulse oximeters are used to measure a blood oxygen saturation level by absorption of light by hemoglobin. In the agricultural field, saccharimeters for measuring the sugar content of fruits by absorption of light by sugar are used.

JP-A-2011-185634 discloses a spectroscopic sensor including a photosensor unit, an angle restricting filter and a spectroscopic filter. The angle restricting filter restricts the incident angle of incident light entering a light-receiving region of the photosensor unit. The spectroscopic filter is formed by a thin multilayer formed on a slope structure provided on the angle restricting filter, The slope structure is formed by a CMP (Chemical Mechanical Polishing) method.

In the above-described spectroscopic sensor, however, it may not be easy to form a slope structure with an accurate angle by the CMP method. Accordingly, there are cases where the spectroscopic filter is not formed easily.

SUMMARY

The invention has been made in view of the technical problem described above. An advantage of some aspects of the invention is to provide a spectroscopic sensor that can be manufactured in a semiconductor process and can improve spectral characteristics, and a method for manufacturing the same.

A method for manufacturing a spectroscopic sensor according to an aspect of the invention includes: (a) forming a light receiving element on a semiconductor substrate; (b) forming an angle restricting filter on the semiconductor substrate after the step (a), the angle restricting filter including a light blocking portion and a first opening and a second opening that are adjacent to each other with the light blocking portion interposed therebetween in plan view of the semiconductor substrate; and (c) forming a spectroscopic filter on the angle restricting filter after the step (b), the spectroscopic filter including a first light transmitting film that has a first thickness and is located at a position that overlaps the first opening in plan view of the semiconductor substrate and a second light transmitting film that has a second thickness different from the first thickness and is located at a position that overlaps the second opening in plan view of the semiconductor substrate, and the step (c) includes: (c1) forming the first light transmitting film having a peripheral edge that overlaps the light blocking portion in plan view of the semiconductor substrate by a lift-off method.; and (c2) forming, after the step (c1), the second light transmitting film at a position spaced apart from the first light transmitting film in plan view of the semiconductor substrate by the lift-off method, the second light transmitting film having a peripheral edge that overlaps the light blocking portion in plan view of the semiconductor substrate.

According to this aspect of the invention, with the use of the lift-off method, the light transmitting films included in the spectroscopic filter can be manufactured with accurate thicknesses by using a semiconductor processing technique, and spectral characteristics can be improved. In addition, because the second light transmitting film is formed at a position spaced apart from the first light transmitting film, the requirement for positioning accuracy between the resist layer for forming the second light transmitting film and the first light transmitting film by the lift-off method can be alleviated.

In the above-described aspect of the invention, it is desirable that in the step (c1), the first light transmitting film is formed such that a distance between a position of the peripheral edge of the first light transmitting film and a position of a peripheral edge of the first opening in plan view of the semiconductor substrate is greater than or equal to a product of a tangent of maximum incident angle of light passing through the angle restricting filter with respect to the semiconductor substrate and a thickness of the spectroscopic filter.

This configuration allows the spectroscopic filter to divide more light in the restriction angle range that can pass through the angle restricting filter.

A method for manufacturing a spectroscopic sensor according to another aspect of the invention includes; (a) forming a light receiving element on a semiconductor substrate; (b) forming an angle restricting filter on the semiconductor substrate after the step (a), the angle restricting filter including a light blocking portion and a first opening and a second opening that are adjacent to each other with the light blocking portion interposed therebetween in plan view of the semiconductor substrate; and (c) forming a spectroscopic filter on the angle restricting filter after the step (b), the spectroscopic filter including a first light transmitting film that has a first thickness and is located at a position that overlaps the first opening in plan view of the semiconductor substrate and a second light transmitting film that has a second thickness different from the first-thickness and is located at a position that overlaps the second opening in plan view of the semiconductor substrate, and the step (c) includes; (c1) forming the first light transmitting film, having a peripheral edge that overlaps the light blocking portion in plan view of the semiconductor substrate by a lift-off method; and (c2) forming, after the step (c1), the second light transmitting film at a position partially overlapping the first light transmitting film in plan view of the semiconductor substrate by the lift-off method, the second light transmitting film having a peripheral edge that overlaps the light blocking portion in plan view of the semiconductor substrate.

According to this aspect of the invention, with the use of the lift-off method, the light transmitting films included in the spectroscopic filter can be manufactured with accurate thicknesses by using a semiconductor processing technique. In addition, because the second light transmitting film is formed at a position that partially overlaps the first light transmitting film, the requirement for positioning accuracy between the resist layer for forming the second light transmitting film and the first light transmitting film by the lift-off method can be alleviated.

A method for manufacturing a spectroscopic sensor according to another aspect of the invention includes; (a) forming a light receiving element on a semiconductor substrate; (b) forming an angle restricting filter that is located on the semiconductor substrate after the step (a); and (c) forming, after the step (b), a spectroscopic filter that is located on the angle restricting filter and includes a first light transmitting film having a first thickness and a second light transmitting film having a second thickness greater than the first thickness, and the step (c) includes: (c1) forming the first light transmitting film by a lift-off method; and (c2) forming the second light transmitting film at a position that is offset from the first light transmitting film in plan view of semiconductor substrate by the lift-off method after the step (c1).

According to this aspect of the invention, the thin first light transmitting film is formed first on the angle restricting filter, and thus in the subsequent step of forming the thick second light transmitting film by the lift-off method, the height difference between the first light transmitting film and the angle restricting filter is relatively small so that the reduction of the positional accuracy when forming the second light transmitting film can be suppressed.

A method for manufacturing a spectroscopic sensor according to another aspect of the invention includes: (a) forming a light receiving element on a semiconductor substrate; (b) forming an angle restricting filter on the semiconductor substrate after the step (a); and (c) forming a spectroscopic filter on the angle restricting filter after the step (b), the spectroscopic filter including a first light transmitting film having a first thickness, a second light transmitting film having a second thickness that is different from the first thickness and a third light transmitting film having a third thickness, and the step (c) includes: (c1) forming the third light transmitting film; (c2) forming the first light transmitting film at a position that overlaps the third light transmitting film in plan view of the semiconductor substrate by a lift-off method after the step (c1); and (c3) forming the second light transmitting film at a position that overlaps the third light transmitting film and is offset from the first light transmitting film, in plan view of the semiconductor substrate by the lift-off method after the step (c2).

According to this aspect of the invention, with the use of the lift-off method, the light transmitting films included in the spectroscopic filter can be manufactured with accurate thicknesses by using a semiconductor processing technique, and spectral characteristics can be improved. Also, after the step (c1) of forming the third light transmitting film, the first light transmitting film is formed at a position that overlaps the third light transmitting film by the lift-off method (c2), and the second light transmitting film is formed at a position that overlaps the third light transmitting film and is offset from, the first light transmitting film by the lift-off method (c3), and therefore if is unnecessary to lift off the third light transmitting film. Accordingly, the light transmitting films that are lifted off may be thin, and thus the thicknesses of the resist layers can also be reduced.

In the above-described aspect of the invention, in the step (c3), the second light transmitting film may be formed at a position that overlaps the third light transmitting film and is spaced apart from the first light transmitting film in plan view of the semiconductor substrate.

With this configuration, the second light transmitting film is formed at a position spaced apart from the first light transmitting film, and therefore the requirement for positioning accuracy between the resist layer for forming the second light transmitting film and the first light transmitting film by the lift-off method can be alleviated.

In the above-described aspect of the invention, in the step (c3), the second light transmitting film may be formed at a position that overlaps the third light transmitting film and partially overlaps the first light transmitting film in plan view of the semiconductor substrate.

With this configuration, because the second light transmitting film is formed at a position that partially overlaps the first light transmitting film, the requirement for positioning accuracy between the resist layer for forming the second light transmitting film and the first light transmitting film by the lift-off method can be alleviated.

In the above-described aspect of the invention, it is desirable that the step (c2) includes forming a fourth light transmitting film that has a fourth thickness and is located at a position that overlaps the first light transmitting film in plan view of the semiconductor substrate, and the step (c3) includes forming a fifth light transmitting film having the fourth thickness and is located at a position that overlaps the second light transmitting film in plan view of the semiconductor substrate.

With this configuration, the fourth light transmitting film can be formed in the same step as the step of forming the first light transmitting film, and the fifth light transmitting film can be formed in the same step as the step of forming the second light transmitting film. Accordingly, it is unnecessary to again set the semiconductor substrate in a film-forming apparatus in order to form the fourth light transmit ting film and the fifth light transmitting film after the first light transmitting film and the second light transmitting film have been formed.

A spectroscopic sensor according to an aspect of the invention includes: a light receiving element located on a semiconductor substrate; an angle restricting filter that is located, on the semiconductor substrate and includes a light blocking portion and a first opening and a second opening that are adjacent to each other with the light blocking portion interposed therebetween in plan view of the semiconductor substrate; and a spectroscopic filter that is located on the angle restricting filter, the spectroscopic filter including a first light transmitting film that has a first thickness and is located at a position that overlaps the first opening in plan view of the semiconductor substrate and a second light transmitting film that has a second thickness different from the first thickness and is located at a position that overlaps the second opening in plan view of the semiconductor substrate, and the first light transmitting film has a peripheral edge that overlaps the light blocking portion in plan view of the semiconductor substrate, and the second light transmitting film is located at a position spaced apart from the first light transmitting film in plan view of the semiconductor substrate and has a peripheral edge that overlaps the light blocking portion in plan view of the semiconductor substrate.

According to this aspect of the invention, the second light transmitting film is located at a position spaced apart from the first light transmitting film, and therefore the requirement for positioning accuracy between the second light transmitting film and the first light transmitting film can be alleviated.

In the above-described aspect of the invention, it is desirable that a distance between a position of the peripheral edge of the first light, transmitting film and a position of a peripheral edge of the first opening in plan view of the semiconductor substrate is greater than or equal to a product, of a tangent of maximum incident angle of light passing through the angle restricting filter with respect to the semiconductor substrate and a thickness of the spectroscopic filter.

This configuration allows the spectroscopic filter to divide more light in the restriction angle range that can pass through the angle restricting filter.

A spectroscopic sensor according to another aspect of the invention includes: a light receiving element located on a semiconductor substrate; an angle restricting filter that is located on the semiconductor substrate and includes a light blocking portion and a first opening and a second opening that are adjacent to each other with the light blocking portion interposed therebetween in plan view of the semiconductor substrate; and a spectroscopic filter that is located on the angle restricting filter, the spectroscopic filter including a first light transmitting film that has a first thickness and is located at a position that overlaps the first, opening in plan view of the semiconductor substrate and a second light transmitting film, that has a second thickness different from the first thickness and is located at a position that overlaps the second opening in plan view of the semiconductor substrate, and the first light transmitting film has a peripheral edge that overlaps the light blocking portion in plan view of the semiconductor substrate, and the second light transmitting film is located at a position that partially overlaps the first light transmitting film in plan view of the semiconductor substrate and has a peripheral edge that overlaps the light blocking portion in plan view of the semiconductor substrate.

According to this aspect of the invention, the second light transmitting film is located at a position that partially overlaps the first light transmitting film, and thus the requirement for positioning accuracy between the second light transmitting film and the first light transmitting film can be alleviated.

In the above-described aspect of the invention, it is desirable that the first light transmitting film has a first thickness, the second light transmitting film has a second thickness that is greater than the first thickness, and the second light transmitting film is located on the first light transmitting film at the peripheral edge overlapping a part of the first light transmitting film.

With this configuration, because a part of the thick, second light transmitting film is located on a part of the thin first light transmitting film, the second light transmitting film is partially bent, but the degree of bending can be made small due to the first light transmitting film being thin.

A spectroscopic sensor according to another aspect of the invention includes: a light receiving element located on a semiconductor substrate; an angle restricting filter that is located on the semiconductor substrate and includes a light blocking portion and a first opening and a second opening that are adjacent to each other with the light blocking portion interposed therebetween in plan view of the semiconductor substrate; and a spectroscopic filter that is located, on the angle restricting filter, the spectroscopic filter including a first light transmitting fills; that has a first thickness and is located at a position, that overlaps the first opening in plan view of the semiconductor substrate, a second light transmitting film that has a second thickness different from the first thickness and is located at a position that overlaps the second opening in plan view of the semiconductor substrate, and a third light transmitting film that has a third thickness and is located so as to extend from a position between the first light transmitting film and the first opening to a position between the second light transmitting film and the second opening, and the first light transmitting film has a peripheral edge that overlaps the light blocking portion in plan, view of the semiconductor substrate, and the second light transmitting film is located at a position spaced apart from the first light transmitting film in plan view of the semiconductor substrate and has a peripheral edge that overlaps the light blocking portion in plan view of the semiconductor substrate.

According to this aspect of the invention, the second light transmitting film is located at a position spaced apart from the first light transmitting film, and therefore the requirement for position accuracy between the second light transmitting film and the first light transmitting film can be alleviated.

In the above-described aspect of the invention, it is desirable that a distance between a position of the peripheral edge of the first light transmitting film and a position of a peripheral edge of the first opening in plan view of the semiconductor substrate is greater than or equal to a product of a tangent of maximum incident angle of light passing through the angle restricting filter with respect to the semiconductor substrate and a thickness of the spectroscopic filter.

This configuration allows the spectroscopic filter to divide more light in the restriction angle range that can pass through the angle restricting filter.

A spectroscopic sensor according to another aspect of the invention includes: a light receiving element located on a semiconductor substrate; an angle restricting filter that is located on the semiconductor substrate and includes a light blocking portion and a first opening and a second opening that are adjacent to each other with the light blocking portion interposed therebetween in plan view of the semiconductor substrate; and a spectroscopic filter that is located on the angle restricting filter, the spectroscopic filter including a first light transmitting film that has a first thickness and is located at a position that overlaps the first opening in plan view of the semiconductor substrate, a second light transmitting film that has a second thickness different from the first thickness and is located at a position that overlaps the second opening in plan view of the semiconductor substrate, and a third light transmitting film that has a third thickness and is located so as to extend from a position between the first light transmitting film and the first opening to a position between the second light transmitting film and the second opening, and the first light transmitting film has a peripheral edge that overlaps the light blocking portion in plan view of the semiconductor substrate, and the second light transmitting film is located at a position that partially overlaps the first light transmitting film in plan view of the semiconductor substrate and has a peripheral edge that overlaps the light blocking portion in plan view of the semiconductor substrate.

According to this aspect of the invention, because the second light transmitting film is located at a position that partially overlaps the first light transmitting film, the requirement, for positioning accuracy between the second light transmitting film and the first light transmitting film can be alleviated.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
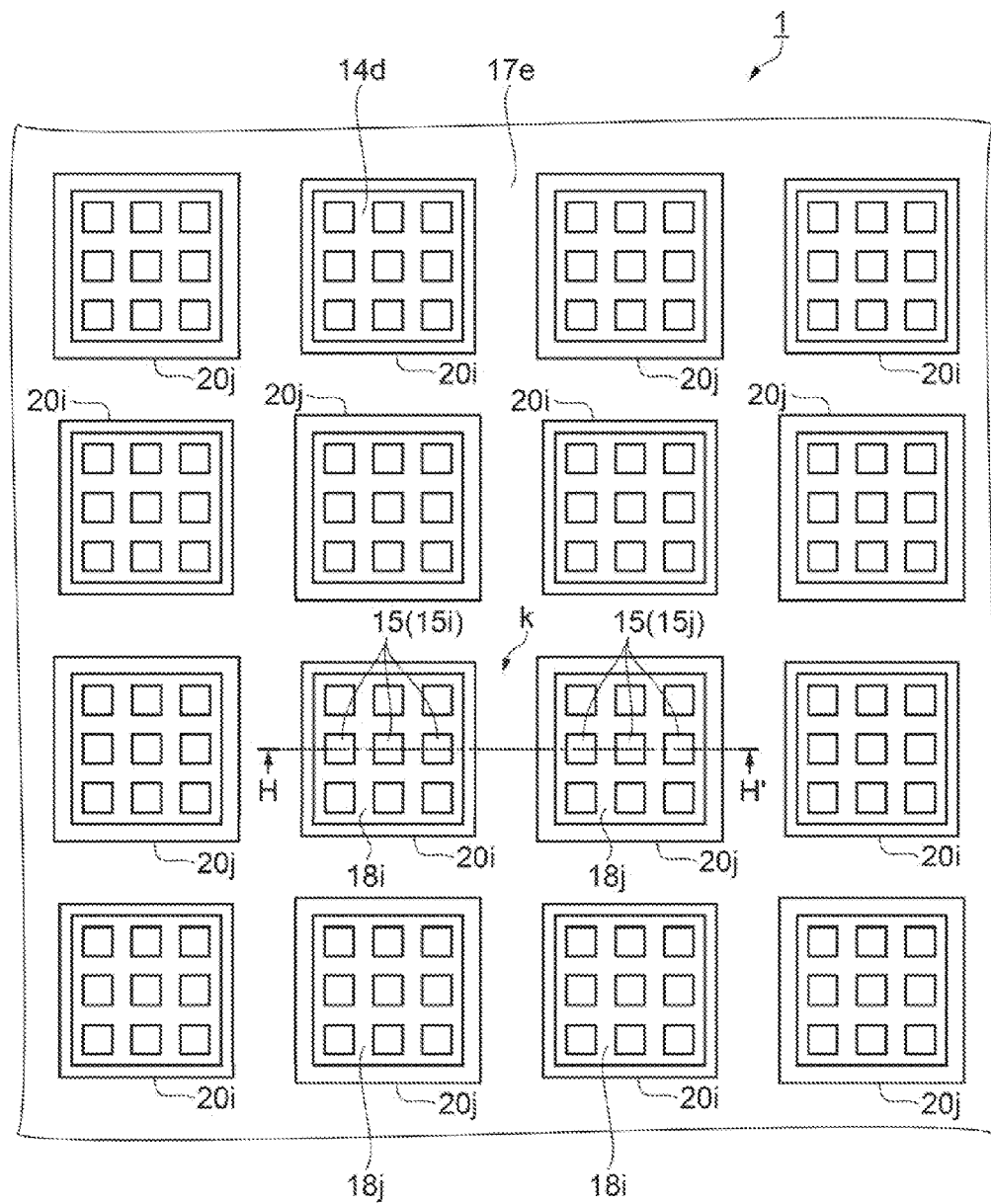
FIG. 1 is a plan view snowing a part of a spectroscopic sensor according to a first embodiment of the invention.

Hereinafter, embodiments of the invention will be described. It is to be understood that the embodiments described below are not intended to unduly limit the scope of the invention recited in the appended claims. It is also to be understood that ail of the constituent elements described in the embodiments are not necessarily required to achieve the means to solve the problems of the invention. It is also to be understood that the same constituent elements are given the same reference numerals, and descriptions thereof are omitted.

First Embodiment
Spectroscopic Sensor

Figure 2:
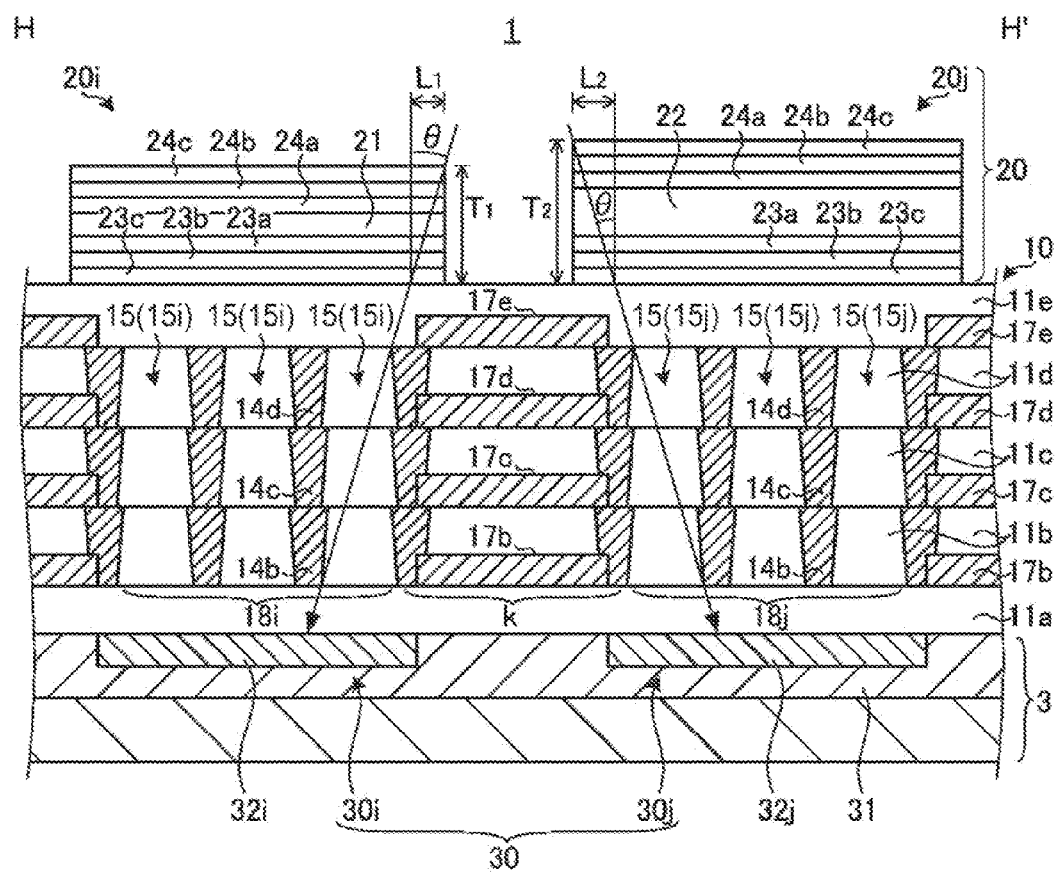
FIG. 2 is a cross-sectional view taken along the line H-H' of FIG. 1.

FIG. 1 is a plan view showing a part of a spectroscopic sensor according to a first embodiment of the invention. FIG. 2 is a cross-sectional view taken along the line H-H' of FIG. 1.

A spectroscopic sensor 1 includes an angle restricting filter 10, a spectroscopic filter 20 and a light receiving element 30 (see FIG. 2).

As shown in FIG. 1, the spectroscopic filter 20 includes first filter units 20$i$ and second filter units 20$j$ that have a rectangular shape in plan view. The first filter units 20$i$ and the second filter units 20$j$ are alternately arranged in rows and columns so as to be adjacent to each other with a light blocking portion k therebetween.

The angle restricting filter 10 includes a plurality of openings 15 that have a rectangular shape in plan view and are arranged so as to correspond to the first filter units 20$i$ and the second filter units 20$j$. As will be described later in detail, light that has passed through the spectroscopic filter 20 passes through the plurality of openings 15 of the angle restricting filter 10 and reaches the light receiving element 30.

Note that the planar shape of the first filter units 20$i$, the second filter units 20$j$ and the openings 15 is not limited to a rectangular shape. Also, in FIG. 2, hatching indicating a cross section of transparent portions is omitted. Hereinafter, constituent elements of the spectroscopic sensor 1 will be described.

Light Receiving Element

The light receiving element 30 is an element that receives light, that has passed through the spectroscopic filter 20 and the angle restricting filter 10 and converts the light into photo-electromotive force. As shown in FIG. 2, the light receiving element 30 includes a first photodiode 30$i$ and a second photodiode 30$j$.

The light receiving element 30 includes various types of semiconductor regions formed on a semiconductor substrate 3 by ion implantation or the like. The semiconductor substrate 3 is formed by, for example, a silicon substrate of second conductivity type. The semiconductor regions formed on the semiconductor substrate 3 include, for example, a first semiconductor region 31 of first conductivity type and second semiconductor regions 32$i$ and 32$j$ of second conductivity type formed in the first semiconductor region 31. In the present embodiment, the first conductivity type is, for example, N type, and the second conductivity type is, for example, P type. However, the K type and the P type may be reversed.

On the semiconductor substrate 3, an electronic circuit (not shown) is formed that applies a predetermined reverse bias voltage to the light receiving element 30, detects a current, produced by a photo-electromotive force generated by the light receiving element 30, and amplifies an analog signal according to the magnitude of the detected current so as to convert the analog signal into a digital signal.

The second semiconductor regions 32$i$ and 32$j$ are respectively connected to a first electrode and a second electrode (not shown). The first semiconductor region 31 is connected to a third electrode (not shown). The first electrode and the third electrode allow a reverse bias voltage to be applied to a P-N junction (the first photodiode 30$i$) formed between the first semiconductor region 31 and the second semiconductor region. 321. The second electrode and the third electrode allow a reverse bias voltage to be applied to a p-N junction (the second photodiode 30$j$) formed between the first semiconductor region 31 and the second semiconductor region 321.

When light that has passed through the spectroscopic filter 20 and the angle restricting filter 10 is received by the light receiving element 30, a photo-electromotive force is generated in the P-N junction formed between the first semiconductor region 31 and the second semiconductor region 321 or 321, and thereby a current is generated. By detecting the current with an electronic circuit connected to the first electrode and an electronic circuit connected, to the second electrode, the light received by the light receiving element 30 can be detected.

Angle Restricting Filter

The angle restricting filter 10 is formed on the semiconductor substrate 3. In the present embodiment, the terms "above" and "on" refer to the direction extending from the semiconductor substrate 3 toward the spectroscopic filter 20 along a thickness direction of the semiconductor substrate 3. Aluminum (Al) alloy layers 17b to 17e are laminated on the semiconductor substrate 3 with each of silicon oxide films 11a to 11having light transmitting properties interposed between adjacent ones of the aluminum alloy layers.

Copper (Cu) alloy layers may be formed in place of the aluminum alloy layers 17b to 17 e.

Each of the aluminum alley layers 17b to 17e has a grid shape in plan view, and includes openings 18I and 18j . In the present embodiment, the term, "plan view" refers to a state as viewed from a direction vertical to the major surface of the semiconductor substrate 3. The opening 18i is located above the first photodiode 30i, and the opening 18j is located above the second photodiode 30j. In each of the openings 18i and 18j of the aluminum alloy layers 17b to 17e, tungsten (W) layers 14b to 14d are located.

Each of the tungsten layers 14b so 14d includes a plurality of openings 15. In the opening 18i of the aluminum alloy layers 17b to 17e, a plurality of openings 15 including first openings 15i are located. In the opening 18j of the aluminum alloy layers 17b to 17e, a plurality of openings 15 including second openings 15I are located. The tungsten layers 14b to 14d are formed on the semiconductor substrate 3 by continuously forming a plurality of layers in a predetermined grid-shaped pattern, for example. This allows the openings 15 formed in each of the tungsten layers 14b to 14d to overlap with each other.

In regions corresponding to the openings 15 of the tungsten layers 14b to 14d, the silicon oxide films 11b to 11d having light transmitting properties mentioned above are located. The openings 15 formed in each of the tungsten layers 14b to 14d form optical paths extending along a lamination direction of the tungsten layers 14b to 14d.

The first opening 15i and the second opening 15j are adjacent to each other with a light blocking portion k interposed therebetween. The light blocking portion k is formed by the aluminum alloy layers 17b to 17e and the tungsten layers 14b to 14d.

The tungsten layers 14b to 14d may be replaced by layers made of a material than has a lower reflectance of light at the wavelength of light to be received by the light receiving element 30 than that of aluminum, and that does not substantially transmit light at the wavelength of light to be received by the light receiving element 30 such as, for example, copper, titanium nitride, titanium, tungsten, titanium, tantalum, tantalum nitride, chromium or molybdenum.

The optical paths formed by the openings 15 of the tungsten layers 14b to 14a restrict the incident angle of light that enters the light receiving element 30. That is, if light enters the optical paths at an inclined angle with respect to the orientation of the optical paths, the light impinges on any one of the tungsten layers 14b to 14d, whereby part of the light is absorbed by any one of the tungsten layers 14b to 14d and the rest of the light is reflected. As a result of being repeatedly reflected while passing through the optical paths, the reflected light is attenuated. Accordingly, the light that can pass through the angle restricting filter 10 is substantially restricted to light whose angle of inclination to the optical paths is less than or equal to a predetermined restriction angle. In the present embodiment, the term "restriction angle" refers to the maximum incident angle of light passing through the angle restricting filter 10 with respect to the semiconductor substrate 3.

In the above-described aspect of the invention, walls are formed as a result of the plurality of tungsten layers 14b to 14d being formed in a predetermined grid-shaped pattern on the semiconductor substrate 3, and thus a fine pattern can be formed, which allows a miniature angle restricting filter 10 to be manufactured. Also, as compared to the case where a spectroscopic sensor is formed by bonding components with an adhesive, the manufacturing process can be simplified, and the reduction of transmitting light due to the adhesive can be suppressed.

In the present embodiment, the angle restricting filter 10 has the optical paths extending in a direction substantially vertical to the semiconductor substrate 3, but the configuration is not limited thereto. The angle restricting filter 10 may have optical paths extending in a direction inclined with respect to the semiconductor substrate 3. In order to form the optical paths extending in a direction inclined with respect to the semiconductor substrate 3, for example, the plurality of tungsten layers 14b to 14d are formed such that each tungsten layer is displaced in a planar direction by a predetermined amount.

Spectroscopic Filter

The spectroscopic filter 20 includes a first filter unit 20i located above the first openings 15i and a second filter unit 20j located above the second openings 15j.

The first filter unit 20i is formed by a plurality of light transmitting films, including titanium oxide films having a high refractive index and silicon oxide films having a low refractive index, that are alternately laminated. To be specific, the first filter unit 20i includes a titanium oxide film 23c, a silicon oxide film 23b, a titanium oxide film 23a, a silicon oxide film 21, a titanium oxide film 24a, a silicon oxide film 24b and a titanium oxide film 24c.

The silicon oxide film 21 corresponds to a first light transmitting film having a first thickness.

The second filter unit 20j is formed by a plurality of light transmitting films, including titanium oxide films having a high refractive index and silicon oxide films having a low refractive index, that are alternately laminated. To be specific, the second filter unit 20j includes a titanium, oxide film 23c, a silicon oxide film 23b, a titanium oxide film 23a, a silicon oxide film 22, a titanium oxide film 24a, a silicon oxide film 24b and a titanium oxide film 24c.

The silicon oxide film 22 corresponds to a second light transmitting film having a second thickness.

The titanium oxide film 23a included, in the first filter unit 20i and the titanium oxide film 23a included in, the second filter unit 20j have the same third thickness. The titanium oxide film 23a corresponds to a third light transmitting film.

The first thickness of the silicon oxide film 21 and the second thickness of the silicon oxide film 22 are determined according to the wavelength of light to be received by the light receiving element 30. The spectroscopic filter 20 restricts the wavelength of light passing through the spectroscopic filter 20 based on the following principle.

To be specific, incident light entering the spectroscopic filter 20 is, when entering the titanium oxide film 23a from the silicon oxide film 21 or 22, split into two parts, namely, reflected light and transmitting light, at an interface between the light transmitting films. Then, part of the reflected light is reflected again at the interface between the silicon oxide film 21 or 22 and the titanium oxide film 24a, and then combined with the transmitting light. At this time, with respect to light having a wavelength that matches the optical path length of the reflected light, the phase of the reflected light and the phase of the transmitting light match, and thus the reflected light and the transmitting light are intensified. With respect to light having a wavelength that does not match the optical path length of the reflected light, the phase of the reflected light and the phase of the transmitting light do not match, and thus the reflected light and the transmitting light are attenuated (interfered).

Here, the optical path length of the reflected light is determined by the incident angle of incident light entering the spectroscopic filter 20. Then, only light having a specific wavelength corresponding to the incident angle of the incident light passes through the spectroscopic filter 20 and exits from the spectroscopic filter 20 at a predetermined exit angle (for example, the same angle as the incident angle with respect to the spectroscopic filter 20).

The angle restricting filter 10 allows only light that has entered the angle restricting filter 10 within a predetermined restriction angle range to pass therethrough. Accordingly, the wavelength of the light that passes through both the spectroscopic filter 20 and the angle restricting filter 10 is restricted to a predetermined range of wavelengths determined based on the thickness of light transmitting films forming the first filter unit 20i or the second filter unit 20j and the restriction angle range of incident light allowed to pass through the angle restricting filter 10.

As described above, because the first filter unit 20i and the second filter unit 20j of the spectroscopic filter 20 respectively include the silicon oxide film 21 and the silicon oxide film 22 having different thicknesses, the first photodiode 30i and the second photodiode 30j can receive light having different wavelengths.

Also, each ox the first filter unit 20i and the second filter unit 20j respectively including the silicon oxide film 21 and the silicon oxide film 22 having different thicknesses can include a titanium oxide film 23a having the same third thickness, a silicon oxide film 23b having the same thickness, a titanium oxide film 23c having the same thickness, a titanium oxide film 24a having the same thickness, a silicon oxide film 24b having the same thickness and a titanium oxide film 24c. having the same thickness. With this configuration, the range of transmitting wavelengths of each of the first filter unit 20i and the second filter unit 20j can be narrowed.

It is desirable that each of the first filter unit 20i and the second filter unit 20j is formed so as to be slightly larger in size than the opening 18i or 18j so that substantially all of the light within the restriction angle range that can pass through the angle restricting filter 10 is divided. Specifically, it is desirable that a distance $L_1$ from a peripheral edge of the first filter unit 20i to a peripheral edge of the first opening 15i in plan view is given by the following Expression 1.

$$L_1 \geq T_1 \cdot \tan\theta, \qquad \text{Expression 1}$$

where $T_1$ represents the thickness of the first filter unit 20i, and $\theta$ represents the restriction angle of the angle restricting filter 10.

Also, it is desirable that a distance $L_2$ from a peripheral edge of the second filter unit 20j to a peripheral edge of the second opening 15j in plan view is given by the following Expression 2.

$$L_2 \geq T_2 \cdot \tan\theta, \qquad \text{Expression 2}$$

where $T_2$ represents the thickness of the second filter unit 20j.

With this configuration, it is possible to increase the amount of light that can be received by the light receiving element 30.

Furthermore, it is desirable that the above-described distances $L_1$ and $L_2$ are determined taking into consideration a positioning margin between the positions of the first opening 15i and the second opening 15j and the position of the spectroscopic filter 20 in the manufacturing process.

If the thickness $T_2$ of the second filter unit 20j is greater than the thickness $T_1$ of the first filter unit 20i, it is desirable that the distance $L_2$ from the peripheral edge of the second filter unit 20j to the peripheral edge of the second opening 15j in plan view is greater than the distance $L_1$ from the peripheral edge of the first filter unit 20i to the peripheral edge of the first opening 15i in plan view.

Method for Manufacturing a Spectroscopic Sensor

Next, a method for manufacturing a spectroscopic sensor 1 according to the present embodiment will be described.

A spectroscopic sensor 1 is manufactured by forming a light receiving element 30 on a semiconductor substrate 3, then forming an angle restricting filter 10 on the light receiving element 30, and then forming a spectroscopic filter 20 on the angle restricting filter 10.

Formation of Light Receiving Element

First of all, a light receiving element 30 is formed on a semiconductor substrate 3. For example, an N-type first semiconductor region 31 is first formed by performing ion implantation or the like on a P-type semiconductor substrate 3. Then, ion implantation or the like is further performed on the first semiconductor region 31 so as to form P-type second semiconductor regions 32i and 32j. This step can be performed at the same time when electronic circuits (not shown) including semiconductor elements are formed on the same semiconductor substrate 3.

Formation of Angle Restricting Filter

Next, an angle restricting filter 10 is formed on the light receiving element 30.

(1) A silicon oxide film 11a is first formed on the semiconductor substrate 3 on which the light receiving element 30 has been formed.

(2) Next, an aluminum alloy layer 11b is formed on a part of the silicon oxide film 11a at the same time when an aluminum alloy layer (not shown) for wiring electronic circuits is formed.

(3) Next, a silicon oxide film 11b is formed on the silicon oxide film 11a and the aluminum alloy layer 17b. The silicon oxide film 11b is formed at the same time when an insulating film (not shown) is formed on the aluminum alloy layer for wiring electronic circuits.

(4) Next, a part of the silicon oxide film 11b is etched so as to form trenches in the silicon oxide film 11b. Next, a tungsten layer 14b is embedded in the trenches formed in the silicon oxide film 11b. The tungsten layer 14b is formed at the same time when a conductive plug (not shown) for interconnecting aluminum alloy layers for multilayer wiring connected to electronic circuits is formed.

(5) Next, an aluminum alloy layer 17c is formed on a part of the silicon oxide film 11b and a part of the tungsten layer 14b at the same rime when an aluminum alloy layer (not shown) for wiring electronic circuits is formed.

(6) Next, a silicon oxide film 11c is formed on the silicon oxide film 11b, the tungsten layer 14b and the aluminum alloy layer 17c. The silicon oxide film 11c is formed at the same time when an insulating film (not shown) is formed on the aluminum alloy layer for wiring electronic circuits.

By repeating the steps (4) to (6) described above a predetermined number of times, an angle restricting filter 10 is formed.

Formation of Spectroscopic Filter

Next, a spectroscopic filter 20 is formed on the angle restricting filter 10.

FIGS. 3 to 8 are cross-sectional views showing a method for manufacturing a spectroscopic sensor according to the first embodiment. FIGS. 3 to 8 show a part corresponding to the part shown in FIG. 2.

Figure 3:
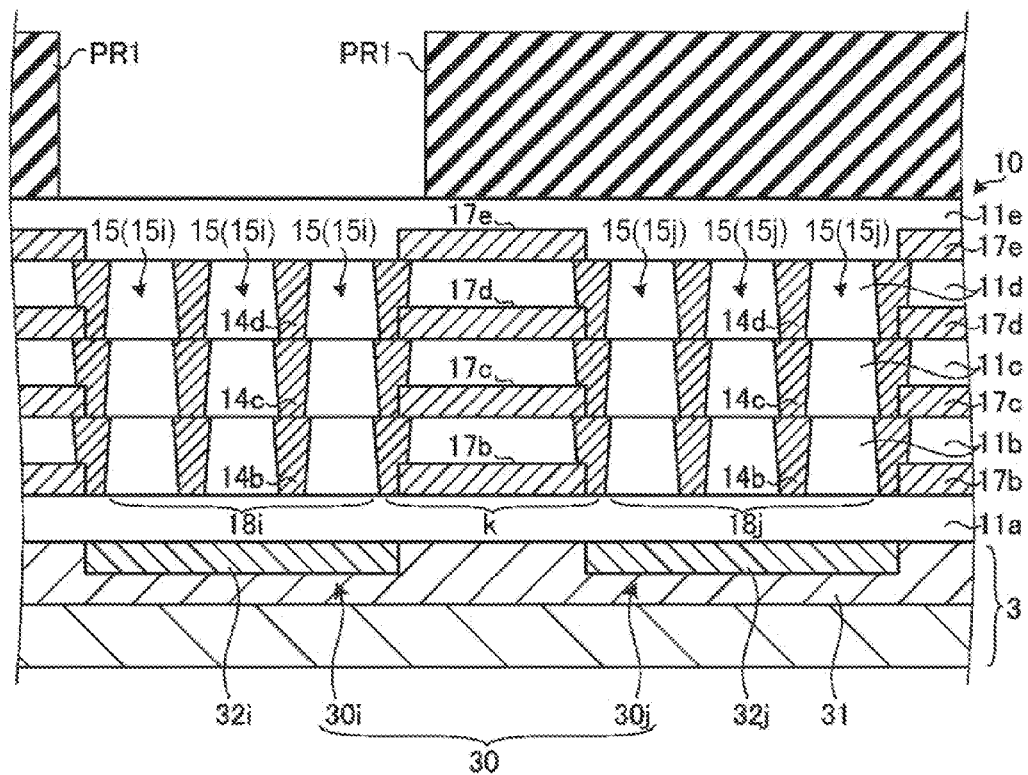
FIG. 3 is a cross-sectional view showing a method for manufacturing a spectroscopic sensor according to the first embodiment.

First, as shown in FIG. 3, a photoresist layer PR1 is formed on the angle restricting filter 10, and then exposed and developed so as to form an opening in the photoresist layer PR1 at a position above the first opening 15$i$.

Figure 4:
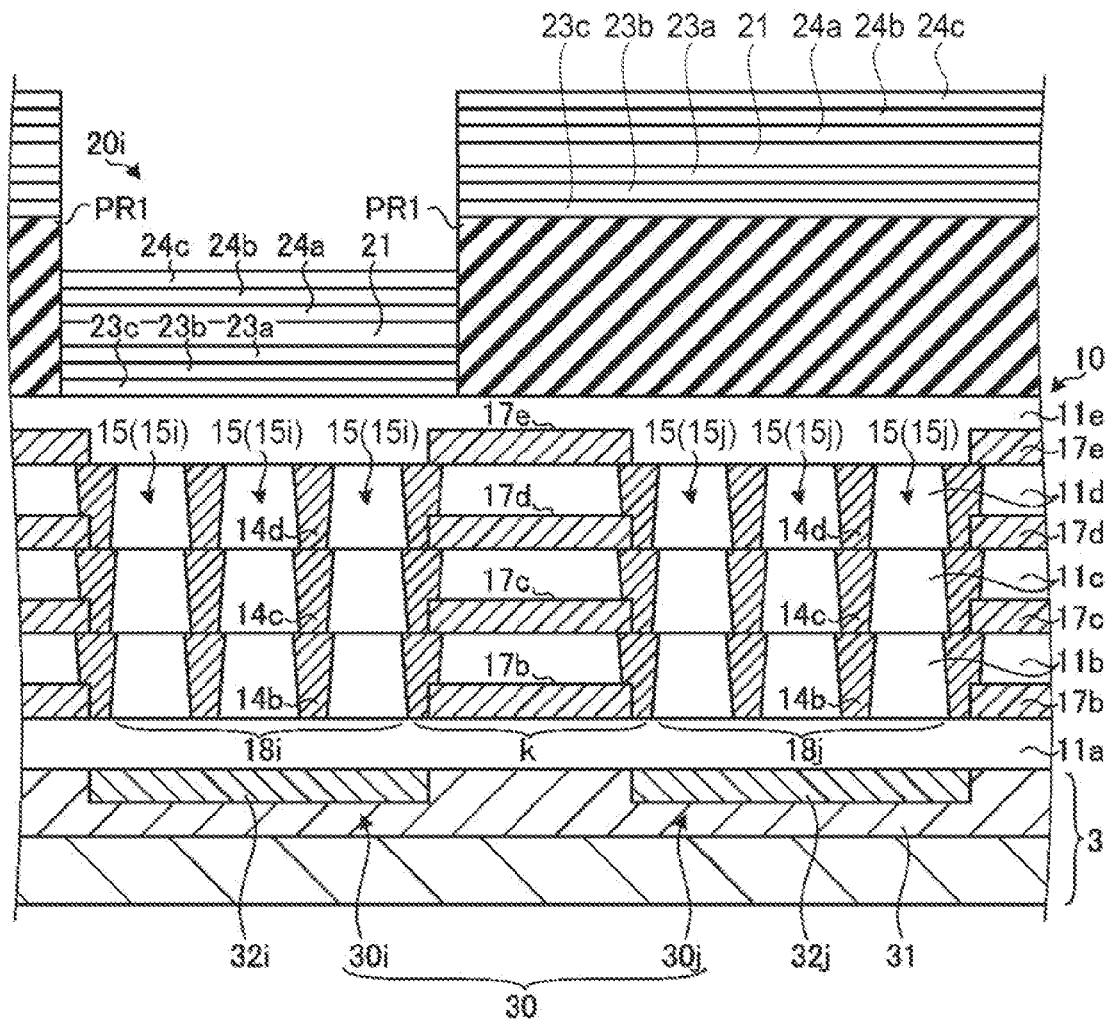
FIG. 4 is a cross-sectional view showing the method for manufacturing a spectroscopic sensor according to the first embodiment.

Next, the semiconductor substrate 3 is set in a film-forming apparatus, then, as shown in FIG. 4, a titanium oxide film 23$c$, a silicon oxide film 23$b$, a titanium oxide film 23$a$, a silicon oxide film 21, a titanium oxide film 24$a$, a silicon oxide film 24$b$ and a titanium oxide film 24$c$ respectively having predetermined thicknesses are formed on the angle restricting filter 10 and the photoresist layer PR1. The thicknesses can be controlled with high accuracy by the film-forming time of the film-forming apparatus.

Figure 5:
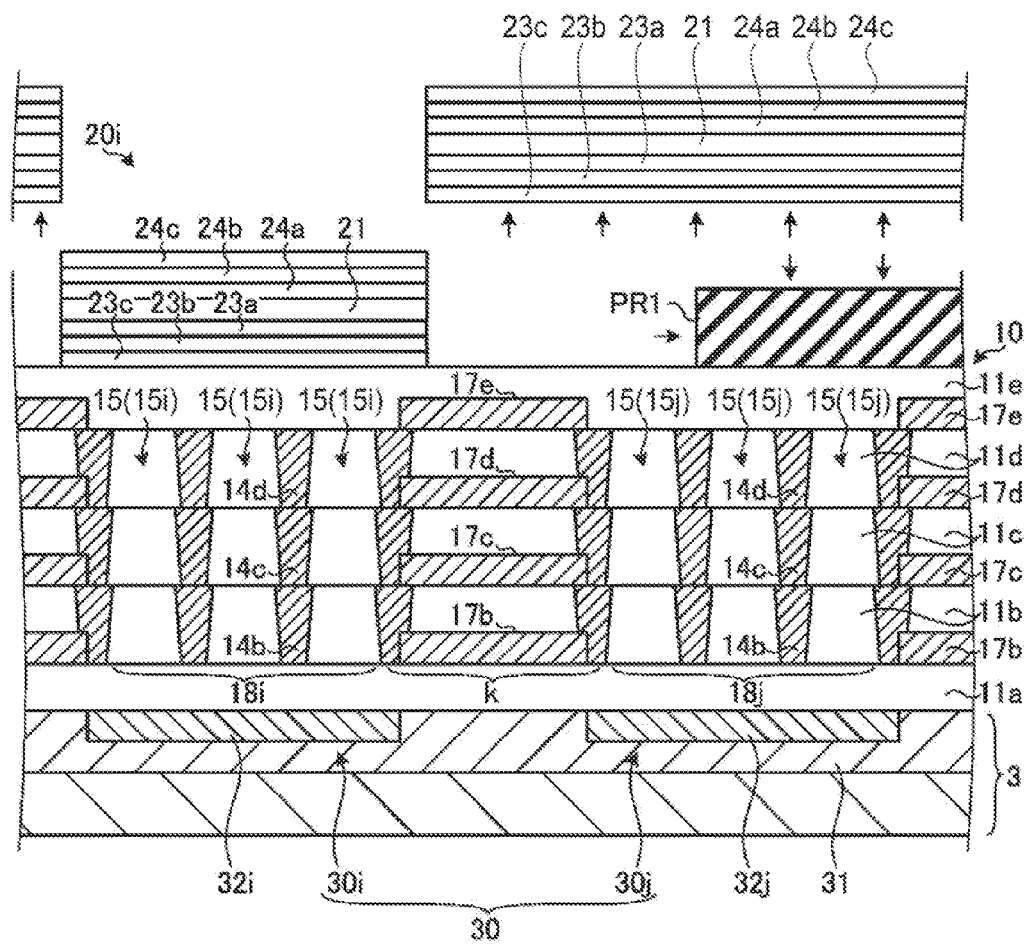
FIG. 5 is a cross-sectional view showing the method for manufacturing a spectroscopic sensor according to the first embodiment.

Next, the semiconductor substrate 3 is taken out of the film-forming apparatus, then, as shown in FIG. 5, the photoresist layer PR1 is stripped off with the use of a stripping liquid. The light transmitting films formed on the photoresist layer PR1 are thereby removed (lifted off), as a result of which the light transmitting films formed on the angle restricting filter 10 remain, and a first filter unit 20$i$ is formed.

Figure 6:
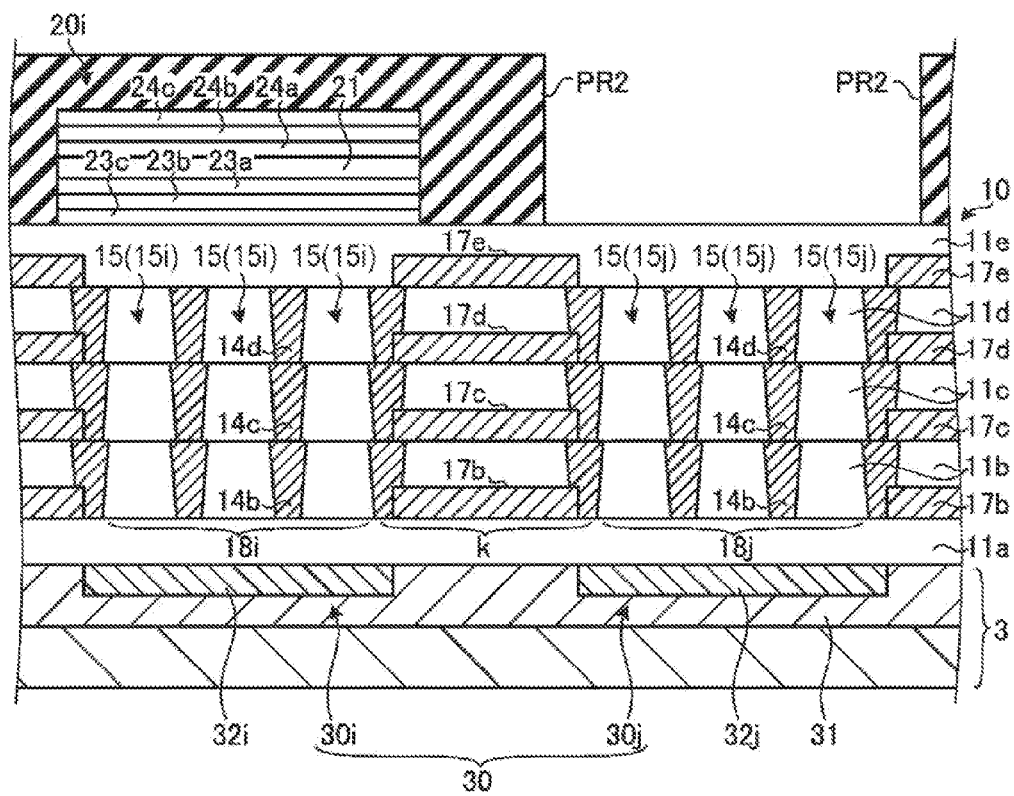
FIG. 6 is a cross-sectional view showing the method for manufacturing a spectroscopic sensor according to the first embodiment.

Next, as shown in FIG. 6, a photoresist layer PR2 is formed on the angle restricting filter 10 and the first filter unit 20$i$, and then exposed and developed so as to form an opening in the photoresist layer PR2 at a position above the second opening 15$j$.

Figure 7:
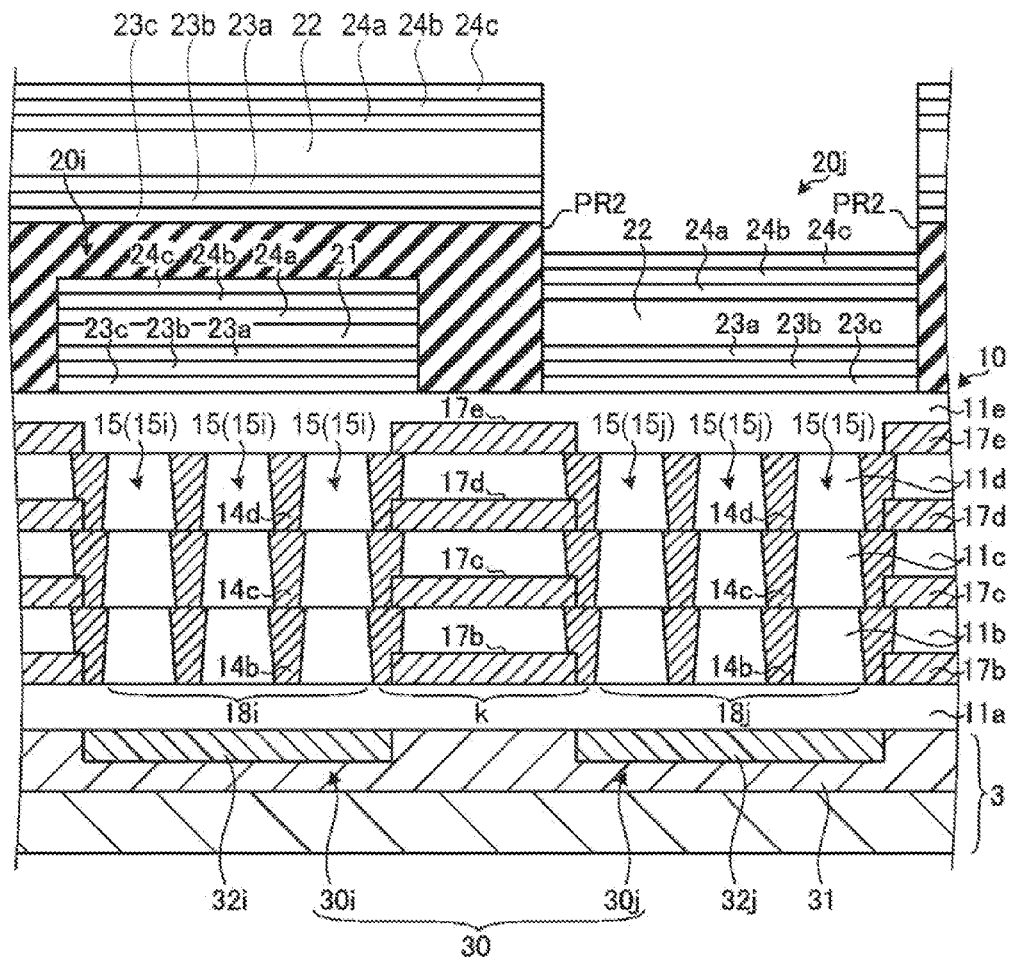
FIG. 7 is a cross-sectional view showing the method for manufacturing a spectroscopic sensor according to the first embodiment.

Next, the semiconductor substrate 3 is set in a film-forming apparatus, then, as shown in FIG. 7, a titanium oxide film 23$c$, a silicon oxide film 23$b$, a titanium oxide film 23$a$, a silicon oxide film 22, a titanium oxide film 24$a$, a silicon oxide film 24$b$ and a titanium oxide film 24$c$ respectively having predetermined thicknesses are formed on the angle restricting filter 10 and the photoresist layer PR2. The thicknesses can be controlled with high accuracy by the film-forming time of the film-forming apparatus.

Figure 8:
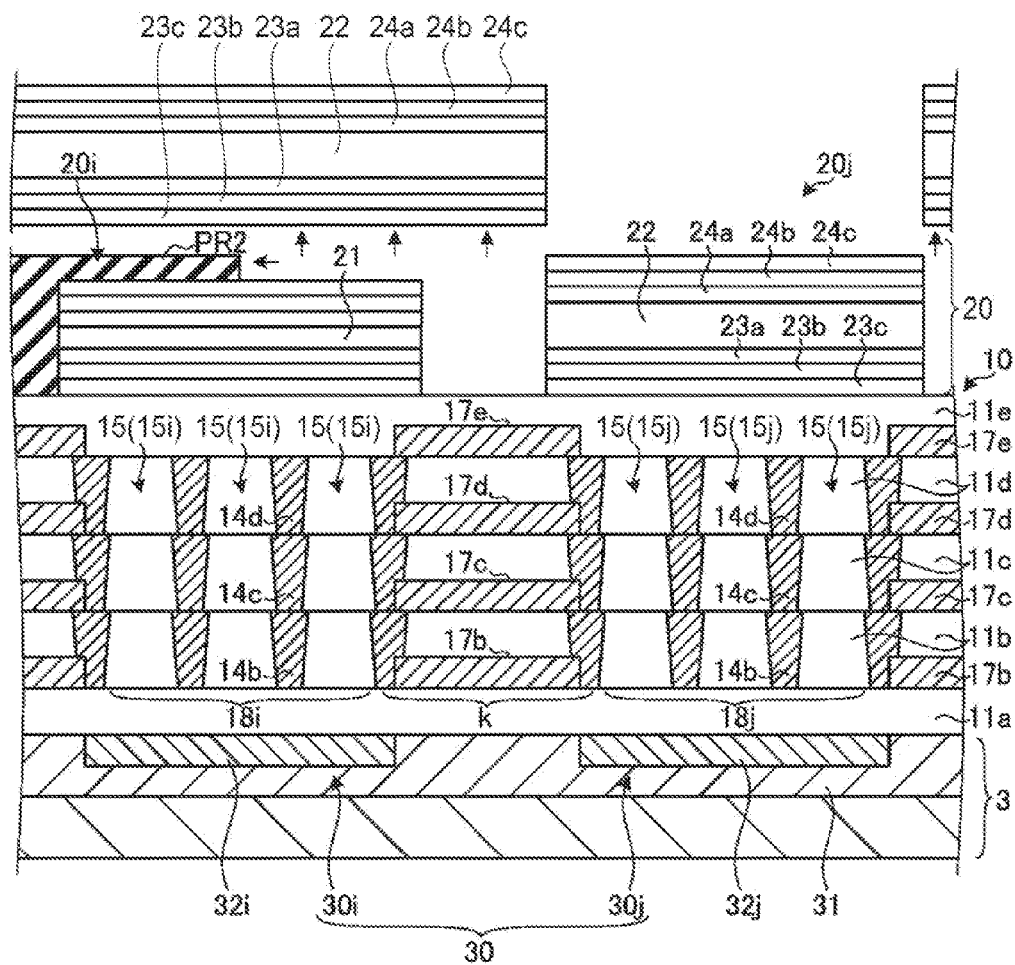
FIG. 8 is a cross-sectional view showing the method for manufacturing a spectroscopic sensor according to the first embodiment.

Next, the semiconductor substrate 3 is taken out of the film-forming apparatus, then, as shown in FIG. 8, the photoresist layer PR2 is stripped off with the use of a stripping liquid. The light transmitting films formed on the photoresist layer PR2 are thereby removed (lifted off), as a result of which the light transmitting films formed on the angle restricting filter 10 remain, and a second filter unit 20$j$ is formed.

Through the above steps, a spectroscopic sensor 1 is manufactured.

The first embodiment described above has the following effects.

(1) According to the spectroscopic sensor 1 and the method for manufacturing a spectroscopic sensor 1, the lift-off method is used, and thus the light transmitting films included in the first filter unit 20$i$ and the second filter unit 20$j$ can be manufactured with accurate thicknesses by a semiconductor processing technique. Also, because the lift-off method is used, the first filter unit 20$i$ including the silicon oxide film 21 having a first thickness and the second filter unit 20$j$ including the silicon oxide film 22 having a second thickness can be made differently without etching the multilayer film.

(2) Also, even if there is a gap between adjacent first filter unit 20$i$ and second filter unit 20$j$, as long as the edge of the first filter unit 20$i$ and the edge of the second filter unit 20$j$ are located above the light blocking portion k, it is possible to prevent the ambient light from entering the first photodiode 30$i$ or the second photodiode 30$j$. In the present embodiment, the second filter unit 20$j$ is formed at a position spaced apart from the first filter unit 20$i$, and thus the position of the opening of the photoresist layer PR2 for forming the second filter unit 20$j$ is not necessarily a position that is in contact with the first filter unit 20$i$. Accordingly, the need to specifically increase the positioning accuracy between the opening of the photoresist layer PR2 and the first filter unit 20$i$ can be reduced.

(3) Also, because the first filter unit 20$i$ including the thin silicon oxide film 21 is formed first, in the subsequent step of forming the second filter unit 20$j$ including the thick silicon oxide film 22 by the lift-off method, the height difference between the first filter unit 20$i$ and the angle restricting filter 10 is relatively small so- that the reduction of the positional accuracy when forming the second filter unit 20$j$ can be suppressed.

Second Embodiment

Spectroscopic Sensor

Figure 9:
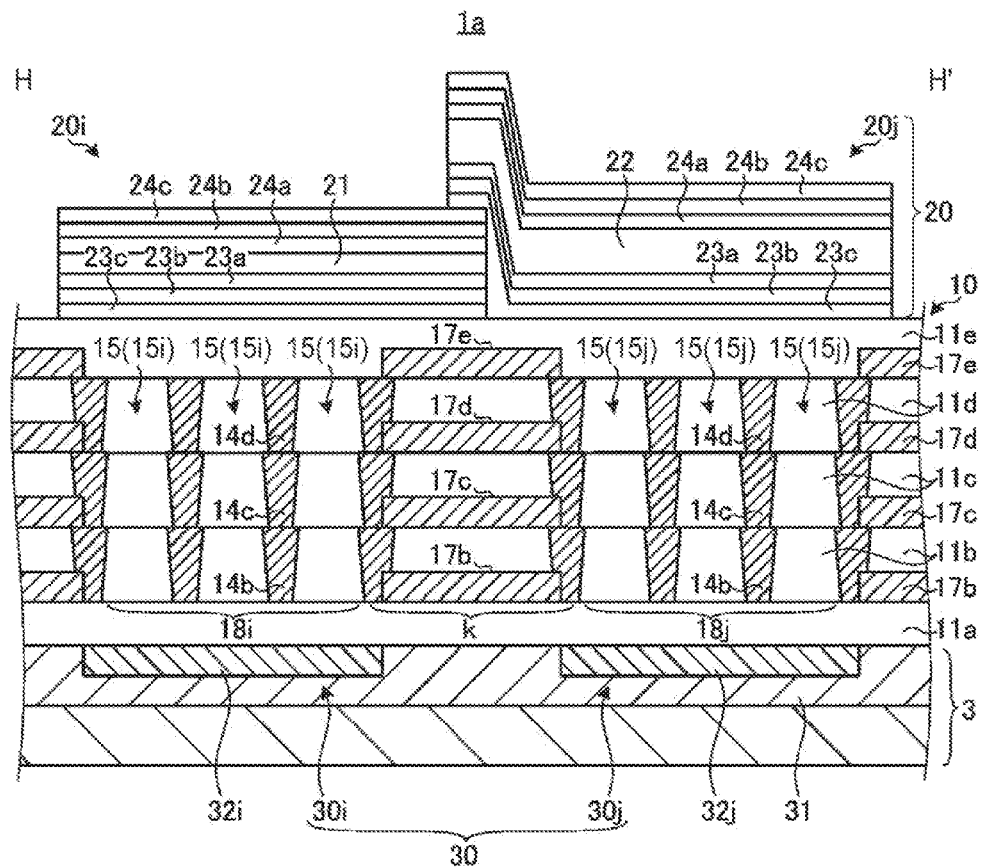
FIG. 9 is a cross-sectional view showing a part of a spectroscopic sensor according to a second embodiment of the invention.

FIG. 9 is a cross-sectional view showing a part of a spectroscopic sensor according to a second embodiment of the invention. FIG. 9 shows a part corresponding to the part shown in FIG. 2.

A spectroscopic sensor 1$a$ according to the second embodiment, is different from the first embodiment in that adjacent first filter unit 20$i$ and second filter unit 20$j$ partially overlap with each other.

In the second embodiment as well, a first filter unit 20$i$ including a thin silicon oxide film 21 is formed first, and thereafter a second filter unit 20$j$ including a thick silicon oxide film 22 is formed. Accordingly, as shown in FIG. 9, in the overlapping portion between the first filter unit 20$i$ and the second filter unit 20$j$, the second filter unit 20$j$ is located on the first filter unit 20$i$, For this reason, the second filter unit 20$j$ is bent at its end, but the first filter unit 20$i$ is relatively thin, and thus the degree of bending is small. Other than this difference, the second embodiment is the same as the first embodiment.

According to the spectroscopic sensor 1$a$ and the method for manufacturing a spectroscopic sensor 1$a$ of the second embodiment, the following effect can be obtained in addition to the effects (1) and (3) obtained by the first embodiment.

(4) Adjacent first filter unit 20$i$ and second filter unit 20$i$ are formed by the lift-off method such that the first filter unit 20$i$ and the second filter unit 20$j$ partially overlap with each other. Accordingly, when the second filter unit 20$j$ is formed, the positioning accuracy between the opening of the photoresist layer PR2 and the first filter unit 20$i$ can be reduced as compared to the first embodiment.

Third Embodiment

Spectroscopic Sensor

Figure 10:
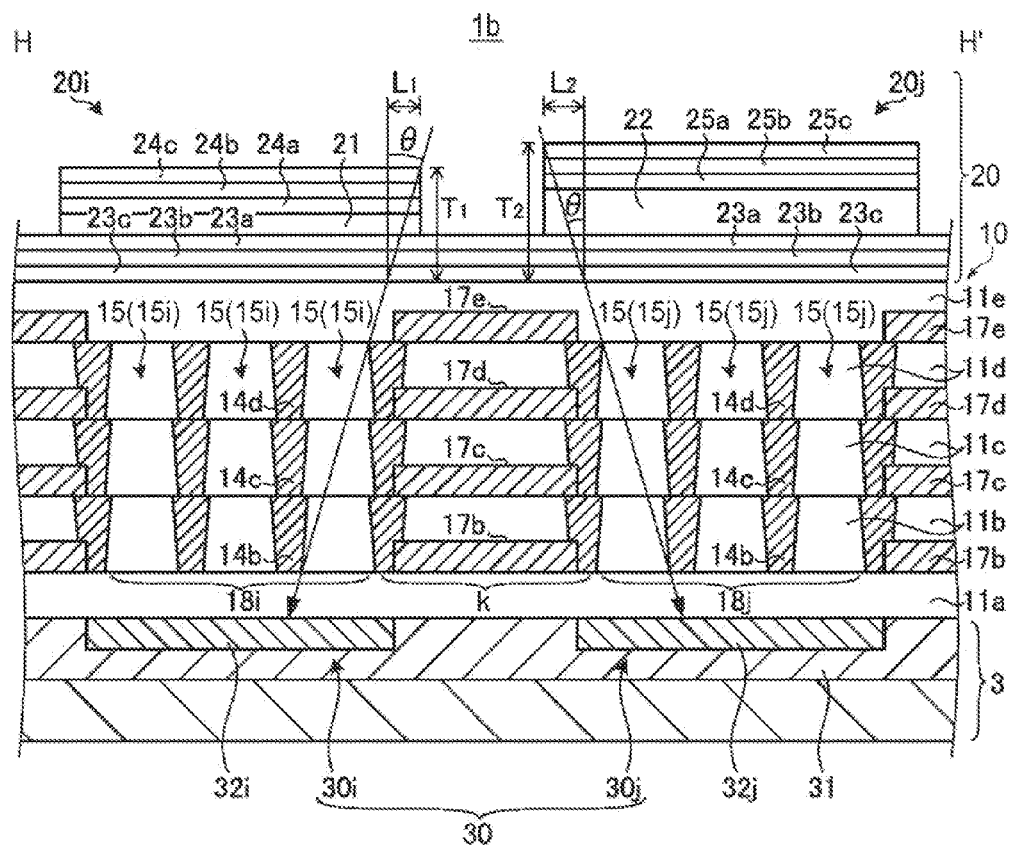
FIG. 10 is a cross-sectional view showing a part of a spectroscopic sensor according to a third embodiment of the invention.

FIG. 10 is a cross sectional view showing a part of a spectroscopic sensor according to a third embodiment of the invention. FIG. 10 shows a part corresponding to the part shown in FIG. 2 illustrating the first embodiment.

A spectroscopic sensor 1$b$ according to the third embodiment is configured by changing the configuration of the spectroscopic filter 20 in the spectroscopic sensor 1 of the first embodiment. Thus, the spectroscopic sensor 1$b$ of the third embodiment is the same as that of the first embodiment except for the above difference. Accordingly, the same reference numerals are given to constituent elements that are the same as those of the spectroscopic sensor 1, and a detailed description thereof is omitted.

As shown in FIG. 10, the spectroscopic sensor 1b of the present embodiment loci cues an angle restricting filter 10, a spectroscopic filter 20 and a light receiving element 30. In FIG. 10, hatching indicating a cross section of transparent portions is omitted. Hereinafter, differences of the spectroscopic filter of the present embodiment from the first embodiment will be described.

Spectroscopic Filter

The spectroscopic filter 20 includes a first filter unit 20i located above first openings 15i and a second filter unit 20j located above second openings 15j. The first filter unit 20i and the second filter unit 20j include a titanium oxide film 23c, a silicon oxide film 23b and a titanium oxide film 23a in common.

The first filter unit 20i is formed by a plurality of light transmitting films, including titanium oxide films having a high refractive index and silicon oxide films having a low refractive index, that are alternately laminated. To be specific, the first filter unit 20i includes, in addition to the titanium oxide film 23c, the silicon oxide film 23b and the titanium oxide film 23a, a silicon oxide film 21, a titanium oxide film 24a, a silicon oxide film 24b and a titanium oxide film 24c. The silicon oxide film 21 corresponds to a first light transmitting film having a first thickness. The titanium oxide film 34a corresponds to a fourth light transmitting film having a fourth thickness.

The second filter unit 20j is formed by a plurality of light transmitting films, including titanium oxide films having a high refractive index and silicon oxide films having a low refractive index, that are alternately laminated. To be specific, the second filter unit 20j includes, in addition to the titanium oxide film 23c, the silicon oxide film 23b and the titanium oxide film 23a, a silicon oxide film 22, a titanium oxide film. 25a, a silicon oxide film 25b and a titanium oxide film 25c. The silicon oxide film 22 corresponds to a second light transmitting film having a second thickness. The titanium oxide film 25a has a fourth, thickness that is the same thickness as the titanium oxide film 24a included in the first filter unit 20i. The titanium oxide film 25a corresponds to a fifth light transmitting film having a fourth thickness.

The titanium oxide film 23a included both in the first filter unit 20i and the second filter unit 20j corresponds to a third light transmitting film having a third thickness.

The first thickness of the silicon oxide film 21 and the second thickness of the silicon oxide film 22 are determined according to the wavelength of light to foe received by the light receiving element 30. The spectroscopic filter 20 restricts the wavelength of light passing through the spectroscopic filter 20 based on the following principle.

To be specific, incident light entering the spectroscopic filter 20 is, when entering the titanium oxide film 23a from, the silicon oxide film 21 or 22, split into two parts, namely, reflected light and transmitting light, at an interface between the light transmitting films. Then, part of the reflected light is reflected again at the interface between the silicon oxide film 21 or 22 and the titanium oxide film 24a or 25a, and then combined with the transmitting light. At this time, with respect to light having a wavelength that matches the optical path length of the reflected light, the phase of the reflected light and the phase of the transmitting light match, and thus the reflected light and the transmitting light are intensified. With respect to light having a wavelength that does not match the optical path length of the reflected light, the phase of the reflected light and the phase of the transmitting light do not match, and thus the reflected light and the transmitting light are attenuated (interfered).

Here, the optical path length of the reflected light is determined by the incident angle of incident light entering the spectroscopic filter 20. Then, only light having a specific wavelength corresponding to the incident angle of the incident light passes through the spectroscopic filter 20 and exits from the spectroscopic filter 20 at a predetermined exit angle (for example, the same angle as the incident angle with respect to the spectroscopic filter 20).

The angle restricting filter 10 allows only light that has entered the angle restricting filter 10 within a predetermined restriction angle range to pass therethrough. Accordingly, the wavelength of the light that passes through both the spectroscopic filter 20 and the angle restricting filter 10 is restricted to a predetermined range of wavelengths determined based on the thickness of light transmitting films constituting the first filter unit 20i or the second filter unit 20j and the restriction angle range of incident light allowed to pass through the angle restricting filter 10.

As described above, because the first filter unit 20i and the second filter unit 20j of the spectroscopic filter 20 respectively include the silicon oxide film 21 and the silicon oxide film 22 having different thicknesses, the first photodiode 30i and the second photodiode 30j can receive light having different wavelengths.

Also, each of the first filter unit 20i and the second filter unit 20j respectively including the silicon oxide film 21 and the silicon oxide film 22 having different thicknesses can include the same titanium, oxide film 23a, the same silicon oxide film 23b, the same titanium oxide film 23c, the titanium oxide films 24a and 25a having the same fourth thickness, the silicon oxide films 24b and 25b having the same thickness and the titanium oxide films 24c and 25c having the same thickness. With this configuration, the range of transmitting wavelengths of each of the first filter unit 20i and the second filter unit 20j can be narrowed.

It is desirable that each of the first filter unit 20i and the second filter unit 20j is formed so as to be slightly larger in size than the opening 18i or 18j so that substantially ail of the light within the restriction angle range that can pass through the angle restricting filter 10 is divided, Specifically, as in the first embodiment, if is desirable that the distance $L_1$ from the peripheral edge of the first filter unit 20i to the peripheral edge of the first opening 15i in plan view is given by the following Expression 1.

$$L_1 \geq T_1 \cdot \tan \theta, \qquad \text{Expression 1}$$

where $T_1$ represents the thickness of the first filter unit 20i, and θ represents the restriction angle of the angle restricting filter 10.

Also, it is desirable that the distance $L_2$ from the peripheral edge of the second filter unit 20j to the peripheral edge of the second opening 15j in plan view is given by the following Expression 2.

$$L_2 \geq T_2 \cdot \tan \theta, \qquad \text{Expression 2}$$

where $T_2$ represents the thickness of the second filter unit 20i.

With this configuration, it is possible to increase the amount of light that can be received by the light receiving element 30.

Furthermore, it is desirable that the above-described distances $L_1$ and $L_2$ are determined taking into consideration a positioning margin between the positions of the first opening 15$i$ and the second opening 15$j$ and the position of the spectroscopic filter 20 in the manufacturing process.

If the thickness $T_2$ of the second filter unit 20$j$ is greater than the thickness $T_1$ of the first filter unit 20$i$, it is desirable that the distance $L_2$ from the peripheral edge of the second filter unit 20$j$ to the peripheral edge of the second opening 15$j$ in plan view is greater than the distance from the peripheral edge of the first filter unit 20$i$ to the peripheral edge of the first opening 15$l$ in plan view.

Method for Manufacturing a Spectroscopic Sensor

Next, a method for manufacturing a spectroscopic sensor 1$b$ according to the present embodiment will be described.

A spectroscopic sensor 1$b$ is manufactured by forming a light receiving element 30 on a semiconductor substrate 3, then forming an angle restricting filter 10 on the light receiving element 30, and then forming a spectroscopic filter 20 on the angle restricting filter 10. The light receiving element 30 and the angle restricting filter 10 can be formed in the same manner as in the first embodiment. Here, a method for forming a spectroscopic filter 20 will be described.

Formation of Spectroscopic Filter

FIGS. 11 to 16 are cross-sectional views showing a method tor manufacturing a spectroscopic sensor according to the third embodiment. FIGS. 11 to 16 show a part corresponding to the part shown in FIG. 10.

Figure 11:
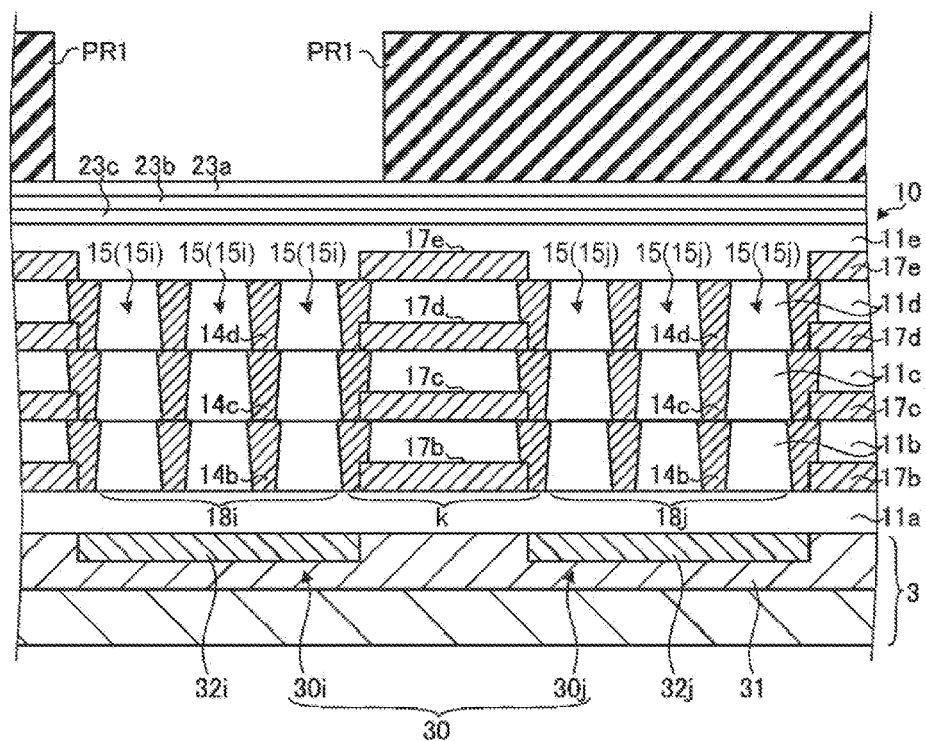
FIG. 11 is a cross-sectional view showing a method for manufacturing a spectroscopic sensor according to the third embodiment.

First, as shown in FIG. 11, a semiconductor substrate 3 is set in a film-forming apparatus, then, a titanium oxide film 23$c$, a silicon oxide film 23$b$ and a titanium oxide film 23$a$ respectively having predetermined thicknesses are formed on the angle restricting filter 10, and thereafter the semiconductor substrate 3 is taken out of the film-forming apparatus. The thicknesses can be controlled with high accuracy by the film-forming time of the film-forming apparatus. Next, a photoresist layer PR1 is formed, and then exposed and developed so as to form an opening in the photoresist layer PR1 at a position above first openings 15$i$.

Figure 12:
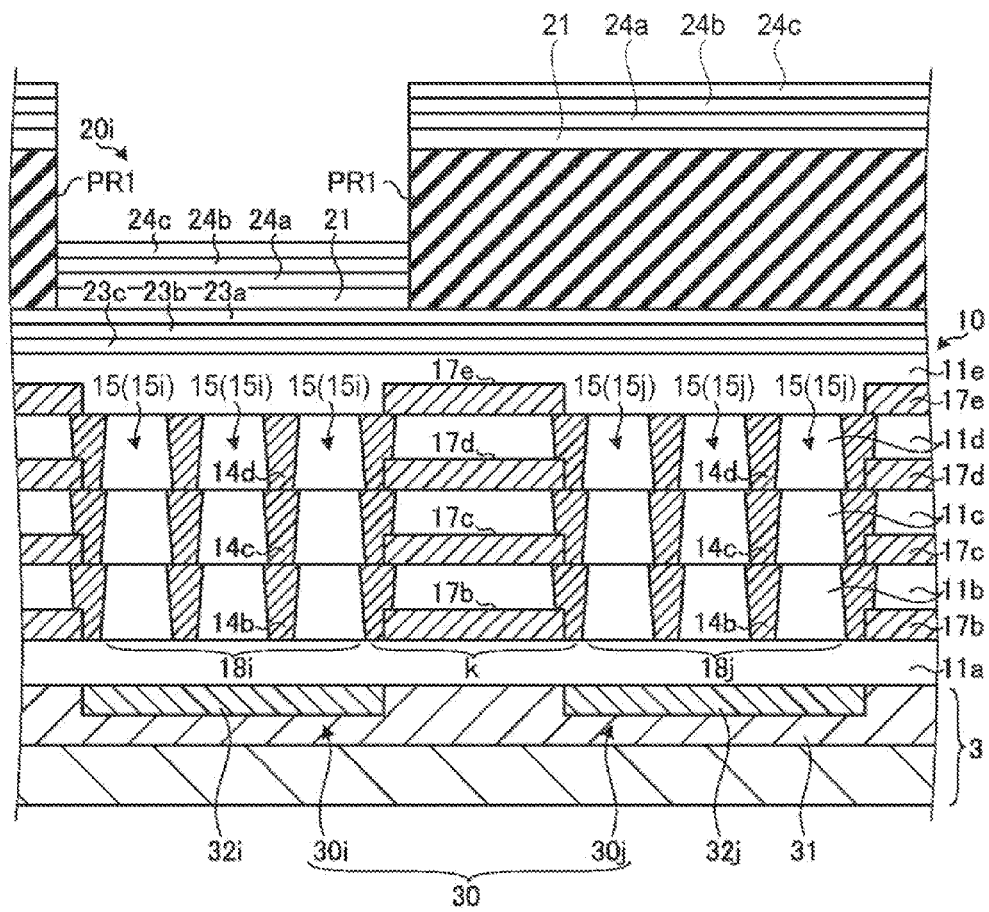
FIG. 12 is a cross-sectional view showing the method for manufacturing a spectroscopic sensor according to the third embodiment.

Next, the semiconductor substrate 3 is set in a film-forming apparatus, then, as shown in FIG. 12, a silicon oxide film 21, a titanium oxide film 24$a$, a silicon oxide film 24$b$ and a titanium oxide film 24$c$ respectively having predetermined thicknesses are formed on the titanium oxide film 23$a$ and the photoresist layer PR1. The thicknesses can be controlled with nigh accuracy by the film-forming time of the film-forming apparatus.

Figure 13:
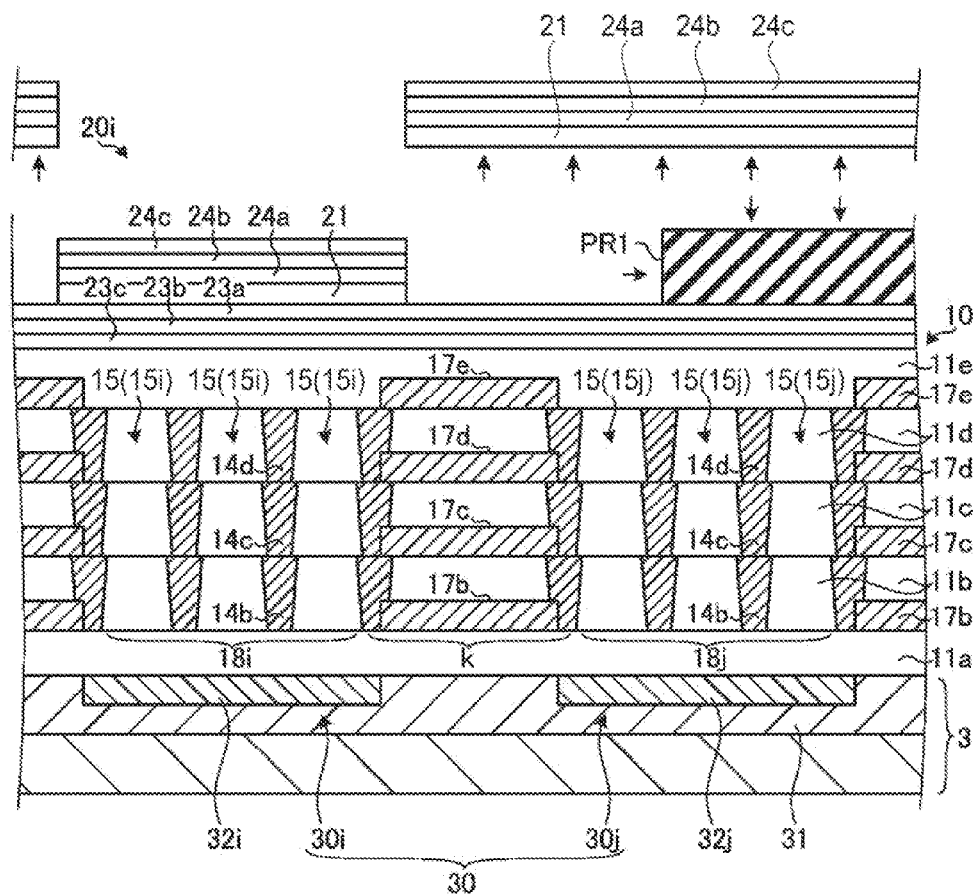
FIG. 13 is a cross-sectional view showing the method for manufacturing a spectroscopic sensor according to the third embodiment.

Next, the semiconductor substrate 3 is taken out of the film-forming apparatus, then, as shown in FIG. 13, the photoresist layer PR1 is stripped off with the use of a stripping liquid. The light transmitting films formed on the photoresist layer PR1 are thereby removed (lifted off), as a result of which the light transmitting films formed on the titanium oxide film 23$a$ remain, and a first filter unit 20$i$ is formed.

Figure 14:
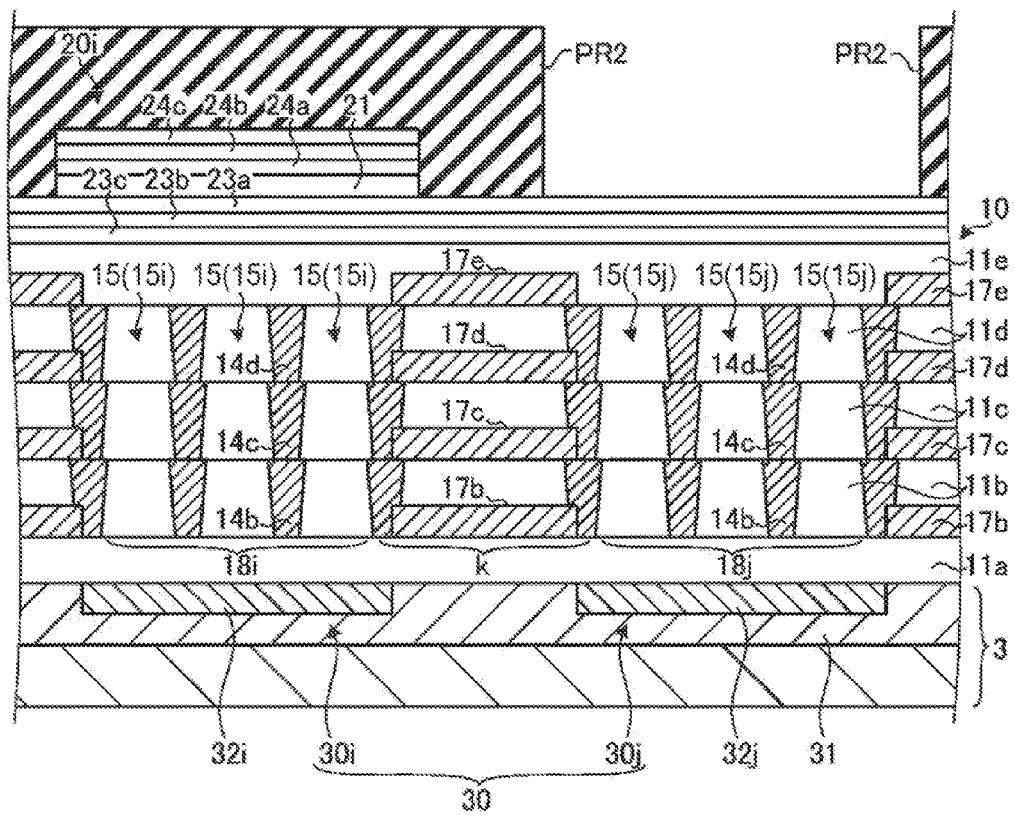
FIG. 14 is a cross-sectional view showing the method for manufacturing a spectroscopic sensor according to the third embodiment.

Next, as shown in FIG. 14, a photoresist layer PR2 is formed on the titanium oxide film 23$a$ and the first filter unit 20$i$, and then exposed and developed so as to form an opening in the photoresist layer PR2 at a position above second openings 15$j$.

Figure 15:
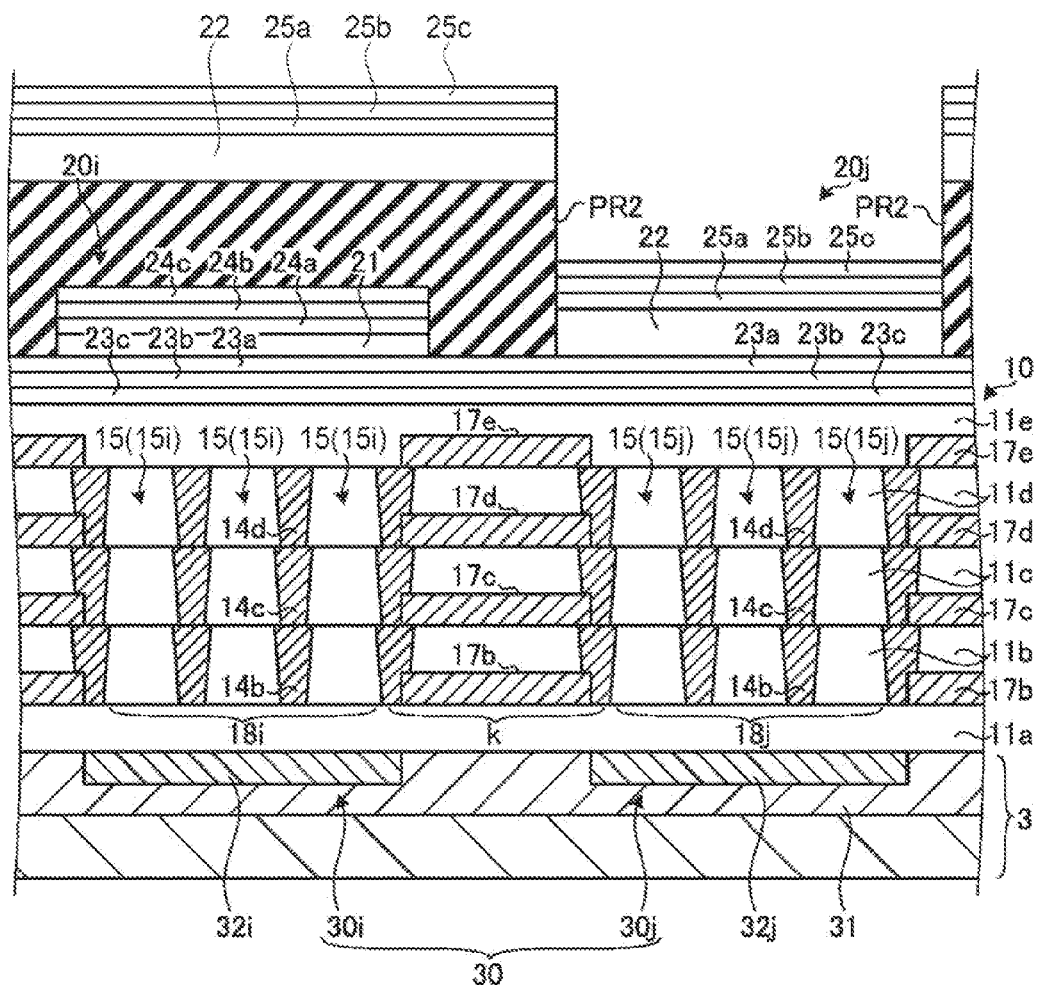
FIG. 15 is a cross-sectional view showing the method for manufacturing a spectroscopic sensor according to the third embodiment.

Next, the semiconductor substrate 3 is set in a film-forming apparatus, then, as shown in FIG. 15, a silicon oxide film 22, a titanium oxide film 25$a$, a silicon oxide film 25$b$ and a titanium oxide film 25$c$ respectively having predetermined thicknesses are formed on the titanium oxide film 23$a$ and the photoresist layer PR2. The thicknesses can be controlled with high accuracy by the film-forming time of the film-forming apparatus.

Figure 16:
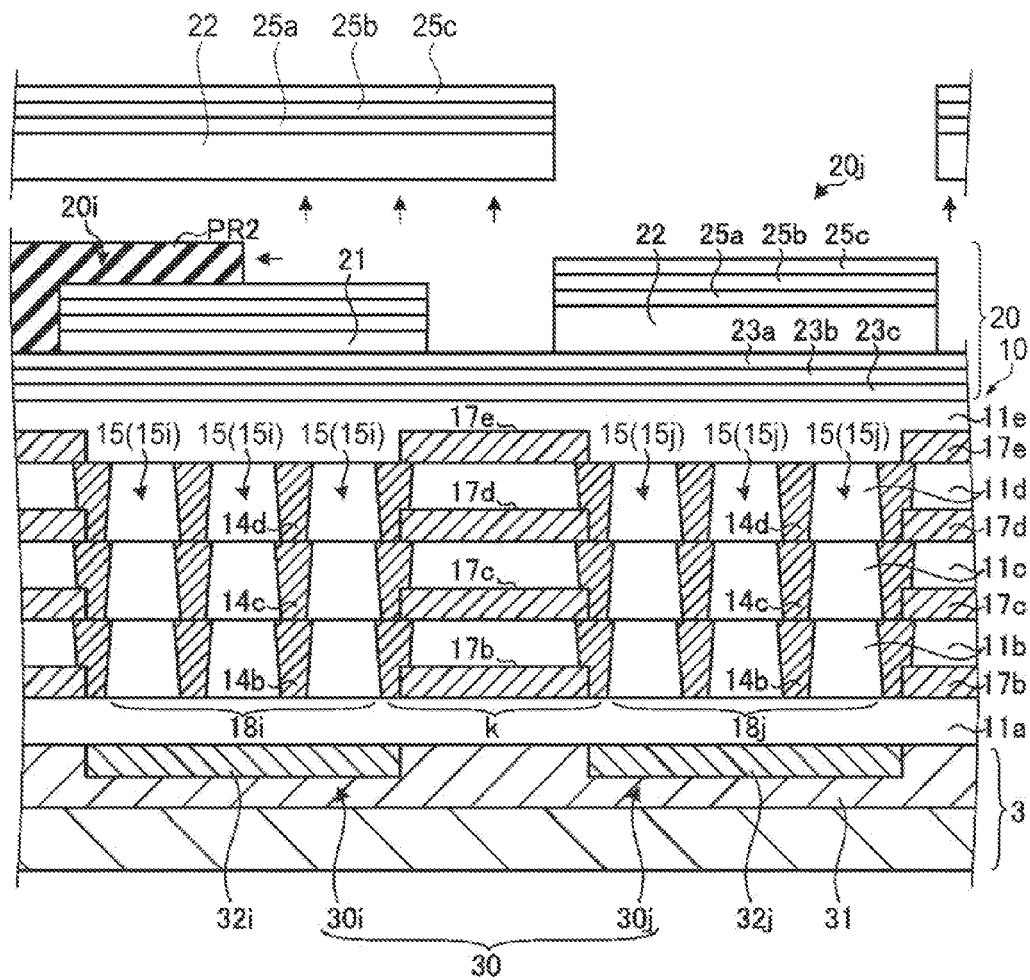
FIG. 16 is a cross-sectional view showing the method for manufacturing a spectroscopic sensor according to the third embodiment.

Next, the semiconductor substrate 3 is taken out of the film-forming apparatus, then, as shown in FIG. 16, the photoresist layer PR2 is stripped off with the use of a stripping liquid. The light transmitting films formed on the photoresist layer PR2 are thereby removed (lifted off), as a result of which the light transmitting films formed on the titanium oxide film 23$a$ remain, and a second filter unit 20$j$ is formed.

Through the above steps, a spectroscopic sensor 1$b$ is manufactured.

According to the spectroscopic sensor 1$b$ and the method for manufacturing a spectroscopic sensor 1$b$ of the third embodiment, the following effects can be obtained in addition to the effects (1) and (2) obtained by the first embodiment.

(5) According to the method for manufacturing a spectroscopic sensor 1$b$, because the thin silicon oxide film 21 that is included in the first filter unit 20$i$ is formed first, in the subsequent step of forming the thick silicon oxide film 22 that is included in the second filter unit 20$j$ by the lift-off method, the height difference between the first filter unit 20$i$ and the titanium oxide film 23$a$ is relatively small so that the reduction of the positional accuracy when forming the silicon oxide film 22 can be suppressed.

(6) Also, after the step of forming the titanium oxide film 23$c$, the silicon oxide film 23$b$ and the titanium oxide film 23$a$, the silicon oxide film 21 is formed, by the lift-off method, and then the silicon oxide film 22 is formed by the lift-off method. Accordingly, it is unnecessary to lift off the titanium oxide film 23$c$, the silicon oxide film 23$b$ and the titanium oxide film 23$a$. Because the light transmitting films that are lifted off may be thin, the thicknesses of the photoresist layers PR1 and PR2 can be reduced, increasing the patterning accuracy of the photoresist layers PR1 and PR2.

(7) Also, the titanium oxide film 24$a$, the silicon, oxide film 24$b$ and the titanium oxide film 24$c$ are lifted off in the same step as the step of lifting off the silicon oxide film 21, and the titanium oxide film 25$a$, the silicon oxide film 25$b$ and the titanium oxide film 25$c$ are lifted off in the same step as the step of lifting off the silicon oxide film 22. Accordingly, it is unnecessary to again set the semiconductor substrate 3 in a film-forming apparatus in order to form the titanium oxide film 24$a$, the silicon oxide film 24$b$, the titanium oxide film 24$c$, the titanium oxide film 25$a$, the silicon oxide film 25$b$ and the titanium oxide film 25$c$ after the silicon oxide films 21 and 22 have been formed.

Fourth Embodiment

Figure 17:
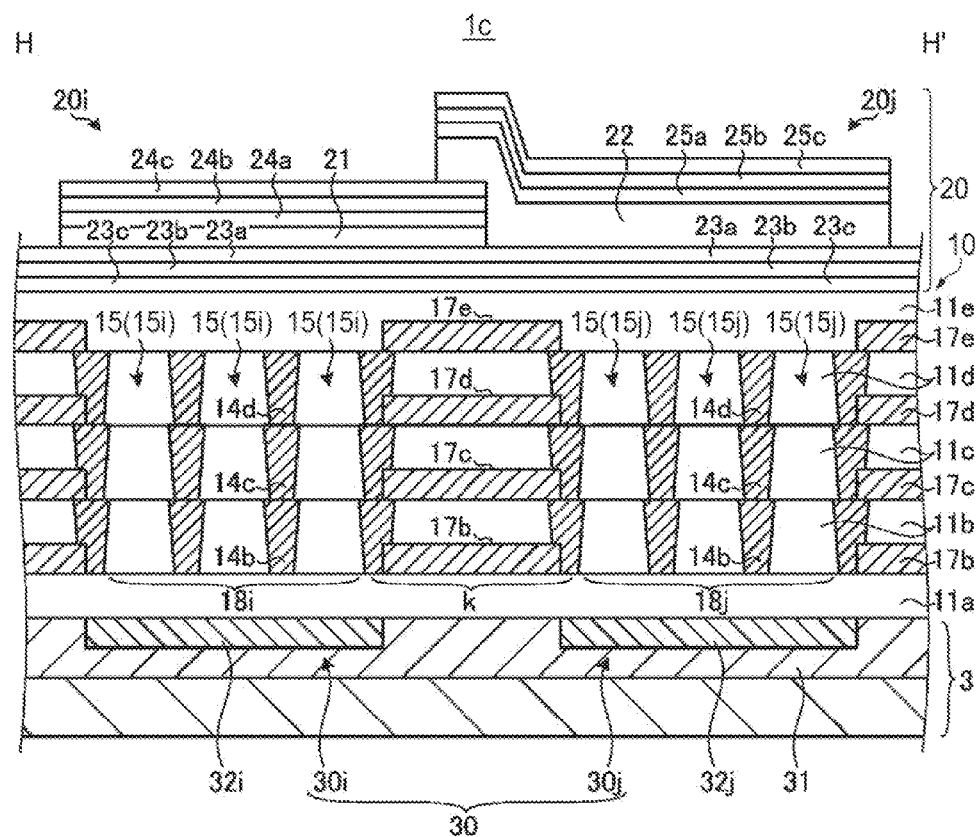
FIG. 17 is a cross-sectional view showing a part of a spectroscopic sensor according to a fourth embodiment of the invention.

FIG. 17 is a cross-sectional view showing a part of a spectroscopic sensor according to a fourth embodiment of the invention. FIG. 17 shows a part corresponding to the part shown in FIG. 10. A spectroscopic sensor be according to the fourth embodiment is different from that of the third embodiment in that the silicon oxide film Si, the titanium oxide film 24$a$, the silicon oxide film 24$b$ and the titanium oxide film 24$c$ included in the first filter unit 20$i$ and the silicon oxide film 22, the titanium oxide film 25$a$, the silicon oxide film 25$b$ and the titanium oxide film 25$c$ included in the second filter unit 20$j$ that is adjacent to the first filter unit 20$i$ partially overlap with each other.

In the fourth embodiment as well, a thin silicon oxide film 21 that is included in a first filter unit 20$i$ is formed first, and thereafter a thick silicon oxide film 22 included in a second filter unit 20$i$ is formed. Accordingly, as shown in FIG. 17, in the overlapping portion between the silicon oxide film 21 and the silicon oxide film 22, the silicon oxide film 22 is located on the silicon oxide film 21. For this reason, the silicon oxide film 22 is bent at its end, but the silicon oxide film 21 is relatively thin, the degree of bending is small. Other than this difference, the fourth embodiment is the same as the third embodiment.

According to the spectroscopic sensor 1c and the method for manufacturing a spectroscopic sensor 1c of the fourth embodiment, the following effect can be obtained in addition to the effects (1), (2), (3), (6) and (7) obtained by the third embodiment.

(8) The silicon oxide film 21, the titanium oxide film 24a, the silicon oxide film 24b and the titanium oxide film 24c that, are included in the first filter unit 20i and the silicon oxide film 22, the titanium oxide film 25a, the silicon oxide film 25b and the titanium oxide film 25c that are included in the second filter unit 20j that is adjacent to the first filter unit 20i are formed by the lift-off method so as to partially overlap with each other. Accordingly, when the silicon oxide film 22, the titanium oxide film 25a, silicon oxide film 25b and the titanium oxide film 25c of the second filter unit 20j are formed, the positioning accuracy between the opening of the photoresist layer PR2 and the first filter unit 20i can be reduced as compared to the third embodiment.

Others

The foregoing description has been given of spectroscopic sensors configured to be capable of detecting light having two types of wavelengths by using the first filter unit 20i and the second filter unit 20j, but the invention is not limited thereto. The spectroscopic sensor may be configured to be capable of detecting, for example, light having three types of wavelengths by further using a third filter unit.

Also, in the above description, the first filter units 20i and the second filter units 20j are arranged in a checkerboard pattern in plan view (see FIG. 1), but they may be arranged in other patterns.

Note that in the invention, the expression "a particular element B (hereinafter referred, to as "B") is formed (or located) on (or under) a particular element A (hereinafter referred to as "A")" is not limited to the case where B is formed (or located) directly on (or under) A. The above expression also encompasses the case where B is formed (or located) on (or under) A with another element interposed therebetween as long as the actions and effects of the invention are not impaired.

What is claimed is:

1. A method for manufacturing a spectroscopic sensor comprising:
    (a) forming a light receiving element on a semiconductor substrate;
    (b) forming an angle restricting filter on the semiconductor substrate after the step (a), the angle restricting filter including a light blocking portion and a first opening and a second opening that are adjacent to each other with the light blocking portion interposed therebetween in plan view of the semiconductor substrate;
    (c) forming a spectroscopic filter on the angle restricting filter after the step (b), the spectroscopic filter including a first filter unit comprising a plurality of light transmitting films that has a first thickness and is located at a position that overlaps the first opening and none of the plurality of light transmitting films of the first filter unit overlap the second opening in plan view of the semiconductor substrate and a second filter unit comprising a plurality of light transmitting films that has a second thickness different from the first thickness and is located at a position that overlaps the second opening and none of the plurality of light transmitting films of the second filter unit overlap the first opening in plan view of the semiconductor substrate; and
    forming the plurality of light transmitting films of the first filter unit such that the plurality of light transmitting film of the first filter unit is spaced apart from the plurality of light transmitting films of the second filter unit in a direction extending along a surface of the angle restricting filter,
    wherein:
    the step (c) includes:
        (c1) forming the first filter unit having a peripheral edge that overlaps the light blocking portion in plan view of the semiconductor substrate by a lift-off method without forming the second filter unit simultaneously; and
        (c2) forming, after the step (c1), the second filter unit at a position spaced apart from the first filter unit in plan view of the semiconductor substrate by the lift-off method without forming the first filter unit simultaneously, the second filter unit having a peripheral edge that overlaps the light blocking portion in plan view of the semiconductor substrate, and
        a first distance between a position of the peripheral edge of the first filter unit to a position of a peripheral edge of the first opening is smaller than a second distance between a position of the peripheral edge of the second filter unit to a position of a peripheral edge of the second opening.

2. The method for manufacturing a spectroscopic sensor according to claim 1,
    wherein in the step (c1), the first filter unit is formed such that a distance between a position of the peripheral edge of the first filter unit and a position of a peripheral edge of the first opening in plan view of the semiconductor substrate is greater than or equal to a product of a tangent of maximum incident angle of light passing through the angle restricting filter with respect to the semiconductor substrate and the first thickness.

3. A method for manufacturing a spectroscopic sensor comprising:
    (a) forming a light receiving element on a semiconductor substrate;
    (b) forming an angle restricting filter on the semiconductor substrate after the step (a), the angle restricting filter including a light blocking portion and a first opening and a second opening that are adjacent to each other with the light blocking portion interposed therebetween in plan view of the semiconductor substrate; and
    (c) forming a spectroscopic filter on the angle restricting filter after the step (b), the spectroscopic filter including a first filter unit comprising a plurality of light transmitting films that has a first thickness and is located at a position that overlaps the first opening and none of the plurality of light transmitting films of the first filter unit overlaps the second opening in plan view of the semiconductor substrate and a second filter unit comprising a plurality of light transmitting films that has a second thickness different from the first thickness and is located at a position that overlaps the second opening and none of the plurality of light transmitting films of the second filter unit overlaps the first opening in plan view of the semiconductor substrate;
    wherein:
    the step (c) includes:
        (c1) forming the first filter unit having a peripheral edge that overlaps the light blocking portion in plan view of the semiconductor substrate by a lift-off method without forming the second filter unit simultaneously; and (c2) forming, after the step (c1), the second filter unit at a position partially overlapping the first filter unit in plan view of the semiconductor substrate by the lift-off method without forming the first filter unit simultaneously, the second filter unit having a peripheral edge that overlaps the light blocking portion in plan view of the semiconductor substrate, and a first distance between a position of the peripheral edge of the first filter unit to a position of a peripheral edge of the first opening is smaller than a second distance between a position of the peripheral edge of the second filter unit to a position of a peripheral edge of the second opening.

4. The method for manufacturing a spectroscopic sensor according to claim 3, wherein in the step (c2), forming the second filter unit at a position partially overlapping the first filter unit only over the light blocking portion in plan view.

5. A method for manufacturing a spectroscopic sensor comprising:

(a) forming a light receiving element on a semiconductor substrate;

(b) forming an angle restricting filter that is located on the semiconductor substrate after the step (a), the angle restricting filter including a light blocking portion and a first opening and a second opening that are adjacent to each other with the light blocking portion interposed therebetween in plan view of the semiconductor substrate;

(c) forming, after the step (b), a spectroscopic filter that is located on the angle restricting filter and includes a first filter unit comprising a plurality of light transmitting films having a first thickness and none of the plurality of light transmitting films of the first filter unit overlaps the second opening, and a second unit having comprising a plurality of light transmitting films having a second thickness greater than the first thickness and none of the plurality of transmitting films of the second filter unit overlaps the first opening; and forming the plurality of light transmitting films of the first filter unit such that the plurality of light transmitting film of the first filter unit is spaced apart from the plurality of light transmitting films of the second filter unit in a direction extending along a surface of the angle restricting filter, wherein:

the step (c) includes:

(c1) forming the first filter unit by a lift-off method without forming the second filter unit simultaneously; and (c2) forming the second filter unit at a position that is offset from the first filter unit in plan view of semiconductor substrate by the lift-off method after the step (c1) without forming the second filter unit simultaneously, and a first distance between a position of the peripheral edge of the first filter unit to a position of a peripheral edge of the first opening is smaller than a second distance between a position of the peripheral edge of the second filter unit to a position of a peripheral edge of the second opening.

* * * * *